United States Patent
Silva et al.

(10) Patent No.: US 12,117,453 B2
(45) Date of Patent: Oct. 15, 2024

(54) PREDICTING PATIENT RESPONSE TO SODIUM CHANNEL BLOCKERS

(71) Applicants: Washington University, St. Louis, MO (US); Istituti Clinici Scientifici Maugeri SpA SB, Castel Goffredo (IT)

(72) Inventors: Jonathan Silva, St. Louis, MO (US); Wandi Zhu, St. Louis, MO (US); Silvia Priori, St. Louis, MO (US); Andrea Mazzanti, St. Louis, MO (US); Kristen Naegle, St. Louis, MO (US)

(73) Assignees: Washington University, St. Louis, MO (US); Istituti Clinici Scientifici Maugeri SpA SB, Castel Goffredo MN (IT)

( * ) Notice: Subject to any disclaimer, the term of this patent is extended or adjusted under 35 U.S.C. 154(b) by 1171 days.

(21) Appl. No.: 16/708,312

(22) Filed: Dec. 9, 2019

(65) Prior Publication Data
US 2020/0182857 A1    Jun. 11, 2020

Related U.S. Application Data

(60) Provisional application No. 62/776,892, filed on Dec. 7, 2018.

(51) Int. Cl.
| | |
|---|---|
| *G01N 33/68* | (2006.01) |
| *C12N 15/10* | (2006.01) |
| *G01N 33/50* | (2006.01) |
| *G05B 23/02* | (2006.01) |
| *G16C 20/30* | (2019.01) |

(52) U.S. Cl.
CPC ....... *G01N 33/6872* (2013.01); *C12N 15/102* (2013.01); *G01N 33/5061* (2013.01); *G05B 23/024* (2013.01); *G16C 20/30* (2019.02); *G01N 2800/52* (2013.01)

(58) Field of Classification Search
USPC .......................................................... 702/19
See application file for complete search history.

(56) References Cited

U.S. PATENT DOCUMENTS

| | | | |
|---|---|---|---|
| 7,094,600 B2* | 8/2006 | Wang | ........... G01N 33/6872 435/325 |
| 7,674,820 B2 | 3/2010 | Fedida et al. | |
| 7,846,968 B2 | 12/2010 | Chien et al. | |
| 8,173,840 B2 | 5/2012 | Chandran | |
| 8,563,776 B2 | 10/2013 | Chandran | |
| 8,660,651 B2 | 2/2014 | Castel et al. | |
| 9,044,482 B2 | 6/2015 | Gupta et al. | |
| 9,375,423 B2 | 6/2016 | Gupta et al. | |
| 9,597,302 B1 | 3/2017 | Yan et al. | |
| 10,004,744 B2 | 6/2018 | Cohen et al. | |
| 2004/0116535 A1 | 6/2004 | Nordmark | |
| 2004/0224960 A1 | 11/2004 | Borchardt et al. | |
| 2005/0070552 A1 | 3/2005 | Fedida et al. | |
| 2006/0135536 A9 | 6/2006 | Fedida et al. | |
| 2006/0241017 A1 | 10/2006 | Chandran | |
| 2006/0287244 A1 | 12/2006 | Chandran | |
| 2007/0010578 A1 | 1/2007 | Chien et al. | |
| 2008/0003214 A1 | 1/2008 | Cezanne et al. | |
| 2009/0325163 A1 | 12/2009 | Helgadottir et al. | |
| 2009/0326607 A1 | 12/2009 | Castel et al. | |
| 2010/0004481 A1 | 1/2010 | Chandran | |
| 2010/0069489 A1 | 3/2010 | Chandran | |
| 2010/0226858 A1 | 9/2010 | Lavedan et al. | |
| 2010/0286762 A1 | 11/2010 | Gourdie et al. | |
| 2011/0009351 A1 | 1/2011 | Thomas et al. | |
| 2012/0027871 A1 | 2/2012 | Wolfgang et al. | |
| 2012/0035215 A1 | 2/2012 | Lavedan et al. | |
| 2012/0058201 A1 | 3/2012 | Lavedan et al. | |
| 2012/0059035 A1 | 3/2012 | Lavedan et al. | |
| 2012/0114670 A1 | 5/2012 | Land et al. | |
| 2012/0289471 A1 | 11/2012 | Chandran | |
| 2013/0189690 A1 | 7/2013 | Dudley | |
| 2014/0051702 A1 | 2/2014 | Gupta et al. | |
| 2015/0225793 A1 | 8/2015 | Lavedan et al. | |
| 2015/0225794 A1 | 8/2015 | Lavedan et al. | |
| 2015/0225795 A1 | 8/2015 | Lavedan et al. | |
| 2015/0246044 A1 | 9/2015 | Cohen et al. | |
| 2015/0290182 A1 | 10/2015 | Gupta et al. | |

(Continued)

FOREIGN PATENT DOCUMENTS

| | | |
|---|---|---|
| EP | 1365757 B1 | 12/2005 |
| EP | 1850841 A1 | 11/2007 |

(Continued)

OTHER PUBLICATIONS

Sobie, Eric A. "Parameter sensitivity analysis in electrophysiological models using multivariable regression." Biophysical journal 96.4 (2009): 1264-1274. (Year: 2009).*

Sobie Supplemental "Parameter sensitivity analysis in electrophysiological models using multivariable regression." Biophysical journal 96.4 (2009): 1264-1274. (Year: 2009).*

Höskuldsson, Agnar. "Variable and subset selection in PLS regression." Chemometrics and intelligent laboratory systems 55.1-2 (2001): 23-38. (Year: 2001).*

Abriel, A. "Cardiac sodium channel Nav1.5 and interacting proteins: Physiology and pathophysiology," Journal of Molecular and Cellular Cardiology, 48(1): 2-11 (2010). doi: 10.1016/j.yjmcc.2009. 08.025.

(Continued)

*Primary Examiner* — G. Steven Vanni
(74) *Attorney, Agent, or Firm* — Armstrong Teasdale LLP

(57) ABSTRACT

Disclosed herein is a method for predicting a patient response to a sodium ion channel blocker such as mexiletine when the patient has LQT syndrome or an arrhythmia. The method generally comprises determining a plurality of parameters associated with sodium ion channels; generating a model for patient response by using a partial least squared (PLS) regression analysis on said plurality of parameters; and using the model to predict the patient response if the patient is administered a sodium ion channel blocker such as mexiletine.

20 Claims, 29 Drawing Sheets

(56) References Cited

U.S. PATENT DOCUMENTS

| | | |
|---|---|---|
| 2015/0307941 A1 | 10/2015 | Salisbury et al. |
| 2015/0368718 A1 | 12/2015 | Wolfgang et al. |
| 2016/0128944 A1 | 5/2016 | Chawrai et al. |
| 2016/0367497 A1 | 12/2016 | Milbrandt et al. |
| 2017/0087105 A1 | 3/2017 | Yan et al. |
| 2018/0068053 A1* | 3/2018 | Barakat .......... G16B 15/00 |

FOREIGN PATENT DOCUMENTS

| | | |
|---|---|---|
| EP | 2121979 A2 | 11/2009 |
| EP | 2134873 A2 | 12/2009 |
| EP | 2152276 A1 | 2/2010 |
| EP | 2416778 A1 | 2/2012 |
| EP | 2416779 A1 | 2/2012 |
| EP | 2417266 A1 | 2/2012 |
| EP | 2417267 A1 | 2/2012 |
| EP | 2661506 A2 | 11/2013 |
| EP | 2705842 A1 | 3/2014 |
| EP | 2892518 A2 | 7/2015 |
| EP | 3003031 A1 | 4/2016 |
| EP | 3023506 A1 | 5/2016 |
| EP | 2819663 B1 | 7/2017 |
| WO | 2002062328 A1 | 8/2002 |
| WO | 2004056180 A1 | 7/2004 |
| WO | 2004056181 A1 | 7/2004 |
| WO | 2005018635 A2 | 3/2005 |
| WO | 2006019984 A2 | 2/2006 |
| WO | 2006078524 A1 | 7/2006 |
| WO | 2007089745 A2 | 8/2007 |
| WO | 2008068780 A2 | 6/2008 |
| WO | 2008121899 A2 | 10/2008 |
| WO | 2008138123 A1 | 11/2008 |
| WO | 2010002517 A1 | 1/2010 |
| WO | 2010117931 A1 | 10/2010 |
| WO | 2010117937 A1 | 10/2010 |
| WO | 2010117941 A1 | 10/2010 |
| WO | 2010117943 A1 | 10/2010 |
| WO | 2011042920 A1 | 4/2011 |
| WO | 2012094651 A2 | 7/2012 |
| WO | 2013127918 A1 | 9/2013 |
| WO | 2014028675 A1 | 2/2014 |
| WO | 2014037416 A2 | 3/2014 |
| WO | 2014195872 A1 | 12/2014 |
| WO | 2016029051 A1 | 2/2016 |
| WO | 2017031342 A1 | 2/2017 |
| WO | 2017053782 A1 | 3/2017 |

OTHER PUBLICATIONS

Becker et al., "Essentials of Local Anesthetic Pharmacology," Anesth Prog 53(3): 98-109 (2006). doi: 10.2344/0003-3006(2006)53[98:EOLAP]2.0.CO;2.

Hanck et al., "Using Lidocaine and Benzocaine to Link Sodium Channel Molecular Conformations to State-Dependent Antiarrhythmic Drug Affinity," Circulation Research, 105(5): 492-499 (2009). doi: 10.1161/CIRCRESAHA.109.198572.

Richards et al., "Examining the Conformational Dynamics of Membrane Proteins in situ with Site-directed Fluorescence Labeling," Journal of Visualized Experiments, 51: e2627 (2011). doi: 10.3791/2627.

Rudokas et al., "The Xenopus Oocyte Cut-open Vaseline Gap Voltage-clamp Technique with Fluorometry," Journal of Visualized Experiments, 85: e51040 (2014). doi: 10.3791/51040.

Wang et al., "Ligand-based design and synthesis of novel sodium channel blockers from a combined phenytoin-lidocaine pharmacophore," Bioorg Med Chem, 17(19): 7064-7072 (2009). doi:10.1016/j.bmc.2008.10.31.

Zhu et al., "Predicting Patient Response to the Antiarrhythmic Mexiletine Based on Genetic Variation," Circulation Research, 124(4): 539-552 (2019). doi: 10.1161/CIRCRESAHA.118.314050.

\* cited by examiner

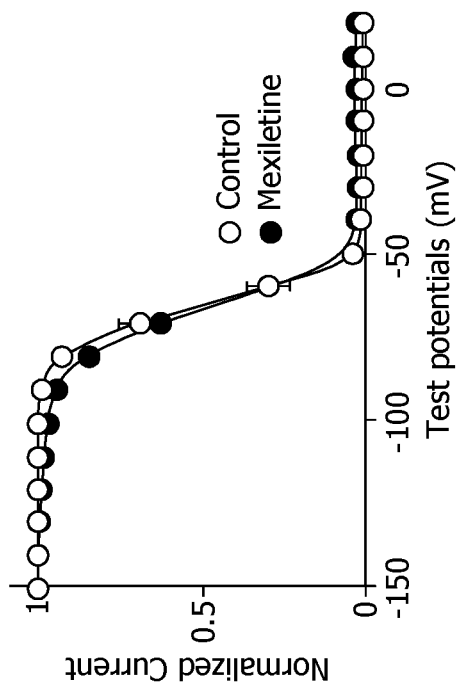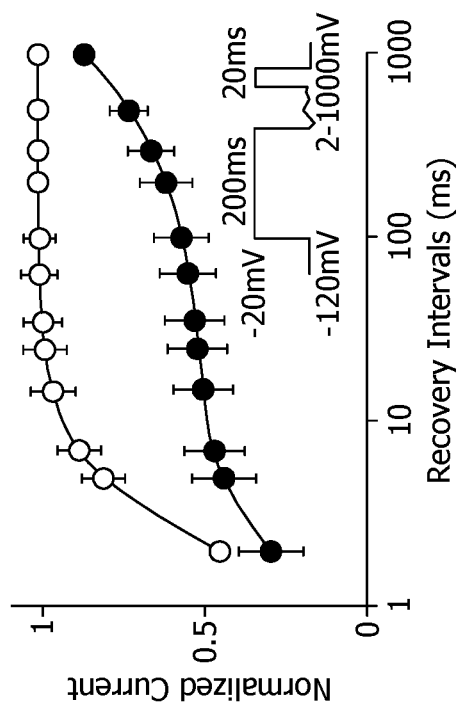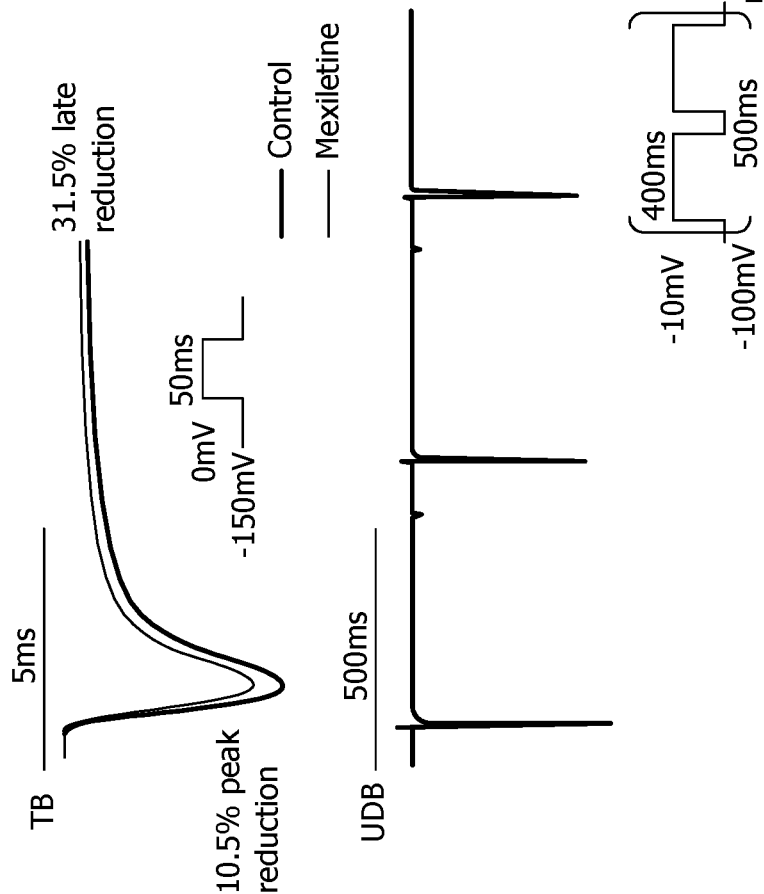
FIG. 1A
FIG. 1B
FIG. 1C

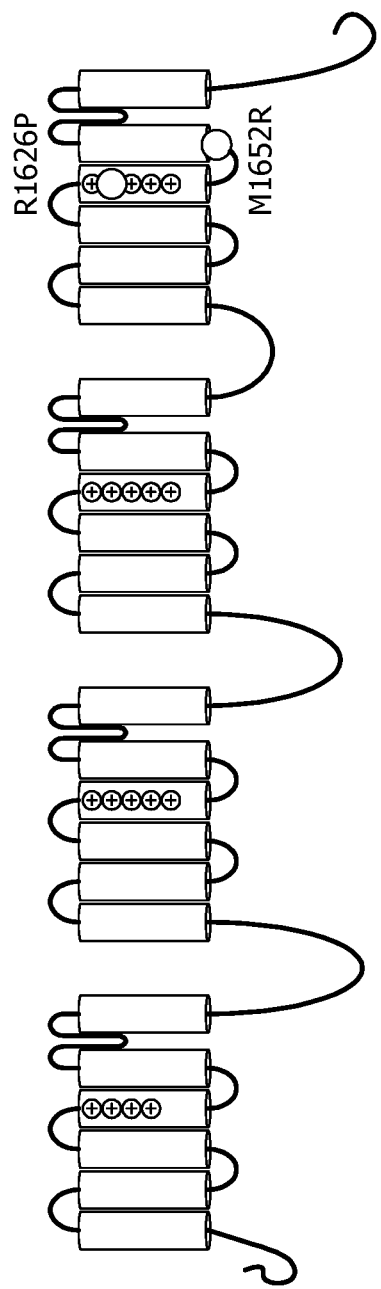
FIG. 2A
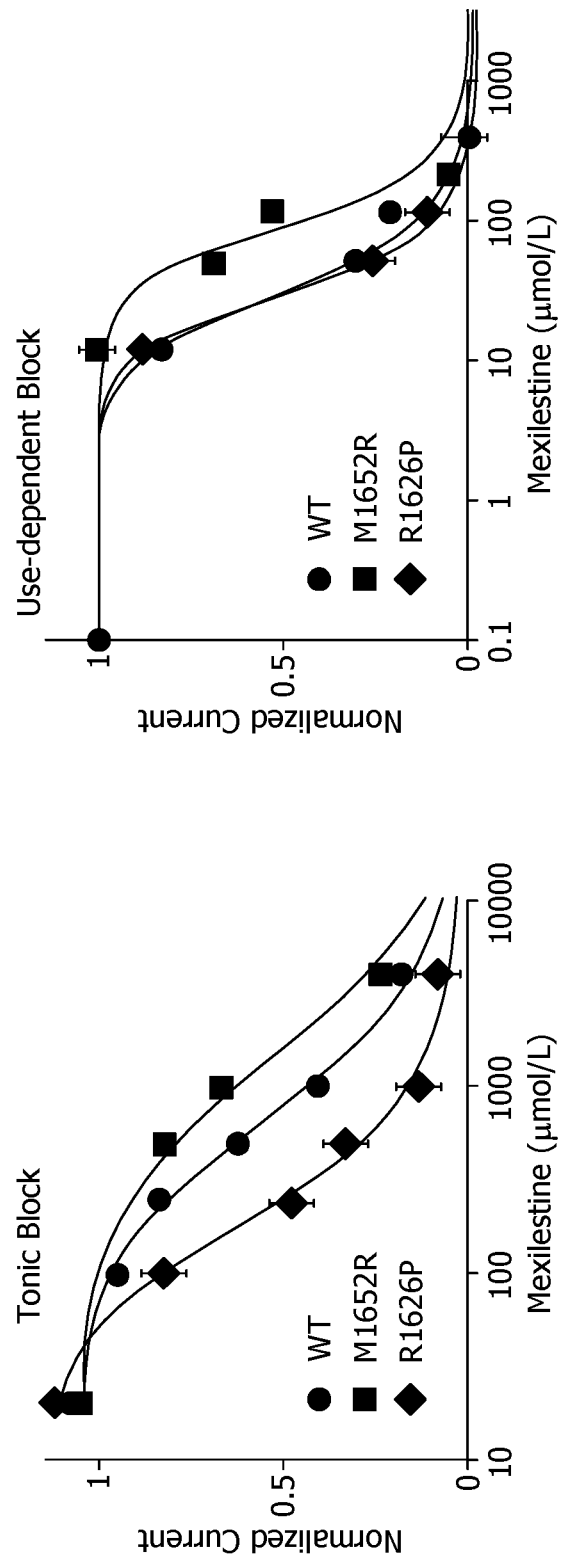
FIG. 2B
FIG. 2C

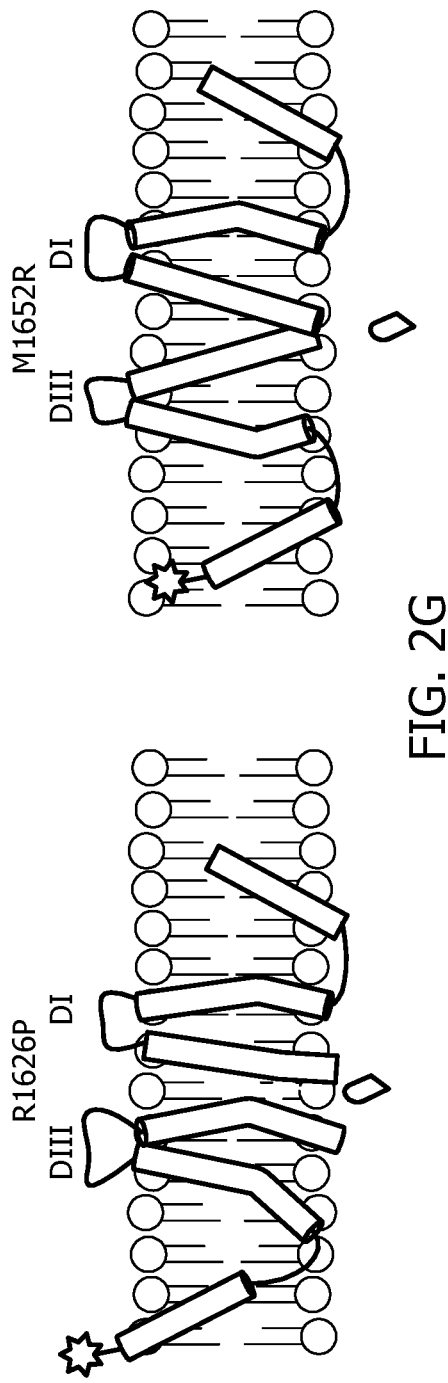
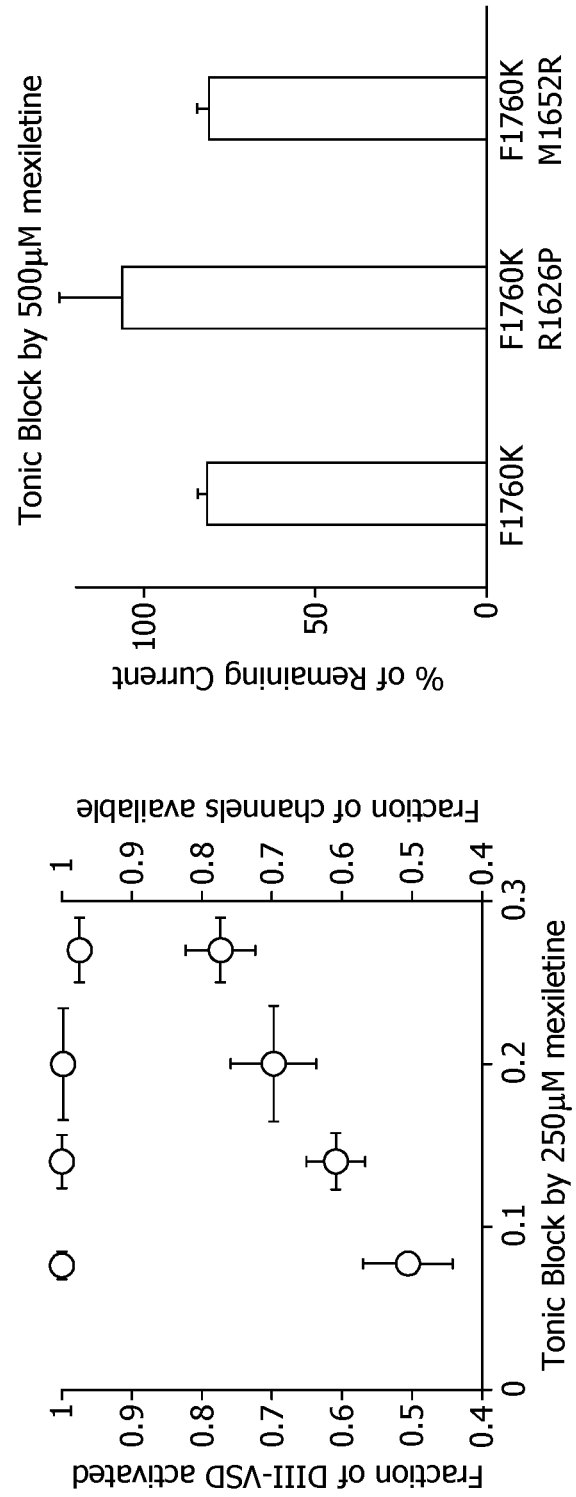
FIG. 2G
FIG. 2H
FIG. 2I

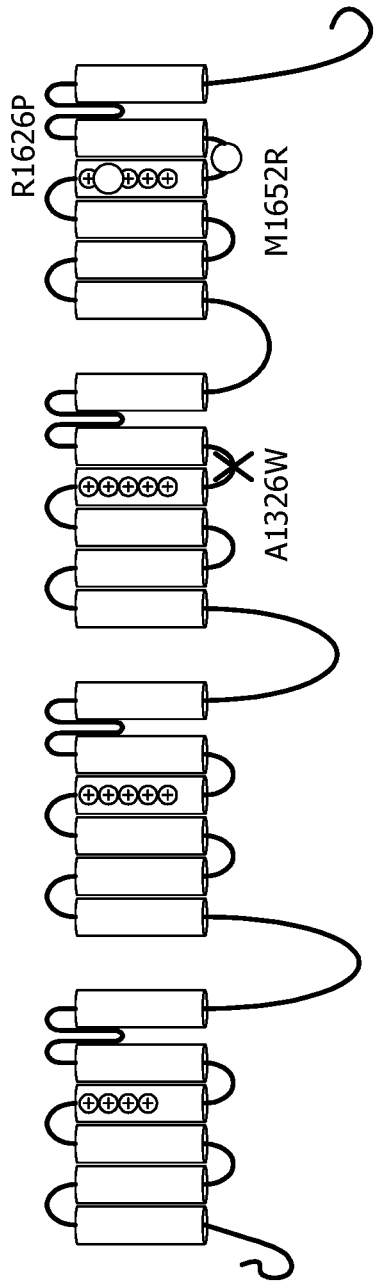
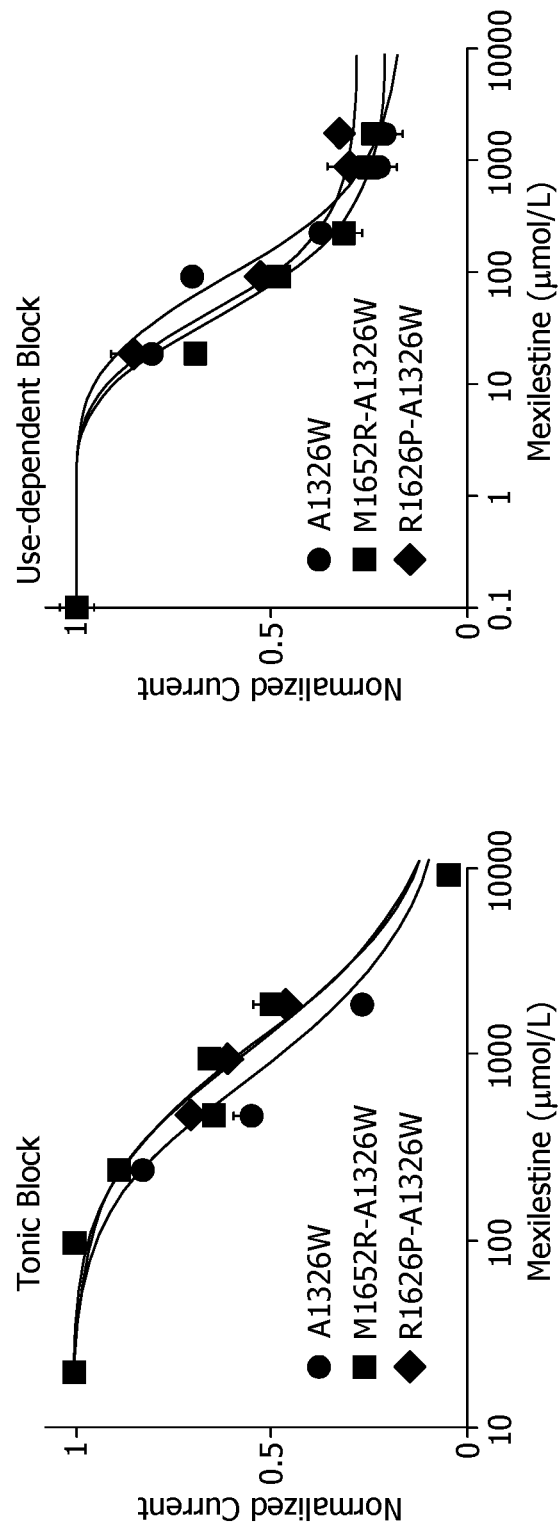
FIG. 3A
FIG. 3B
FIG. 3C

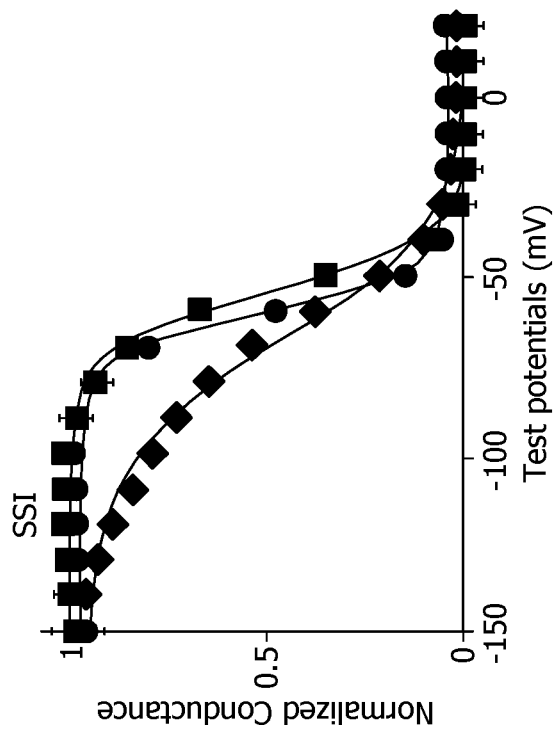
FIG. 3D
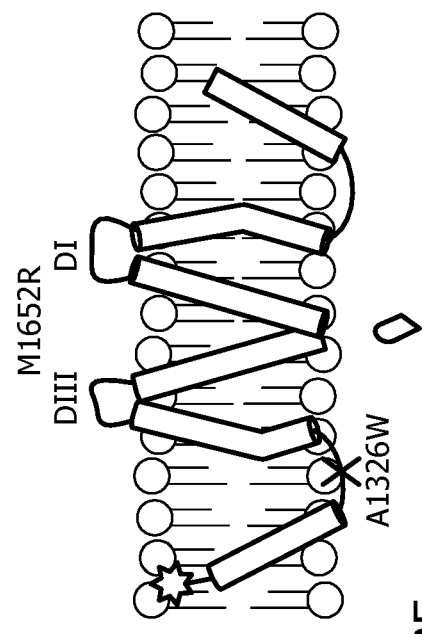
FIG. 3E
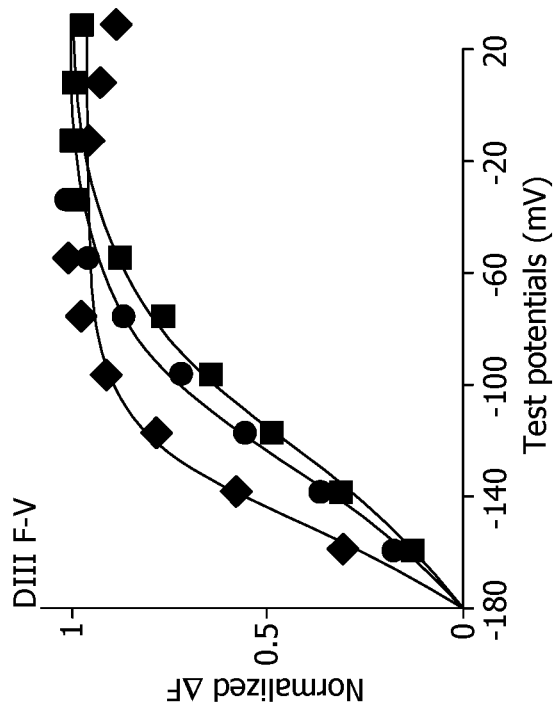
FIG. 3F
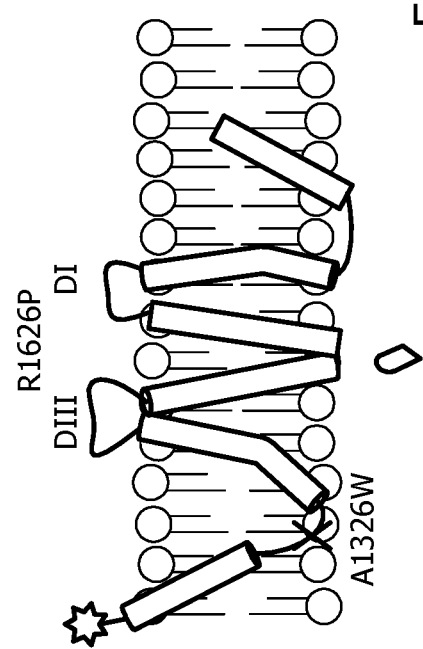

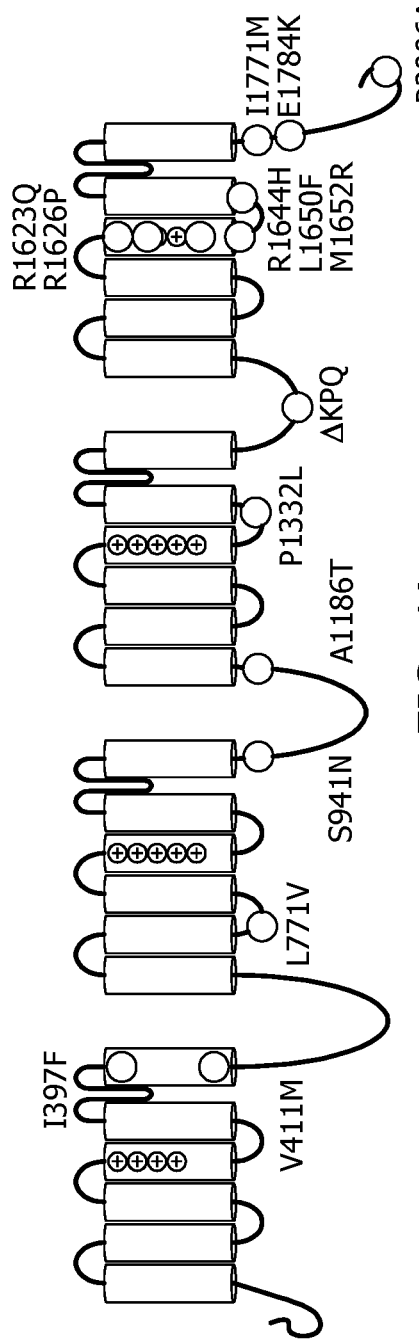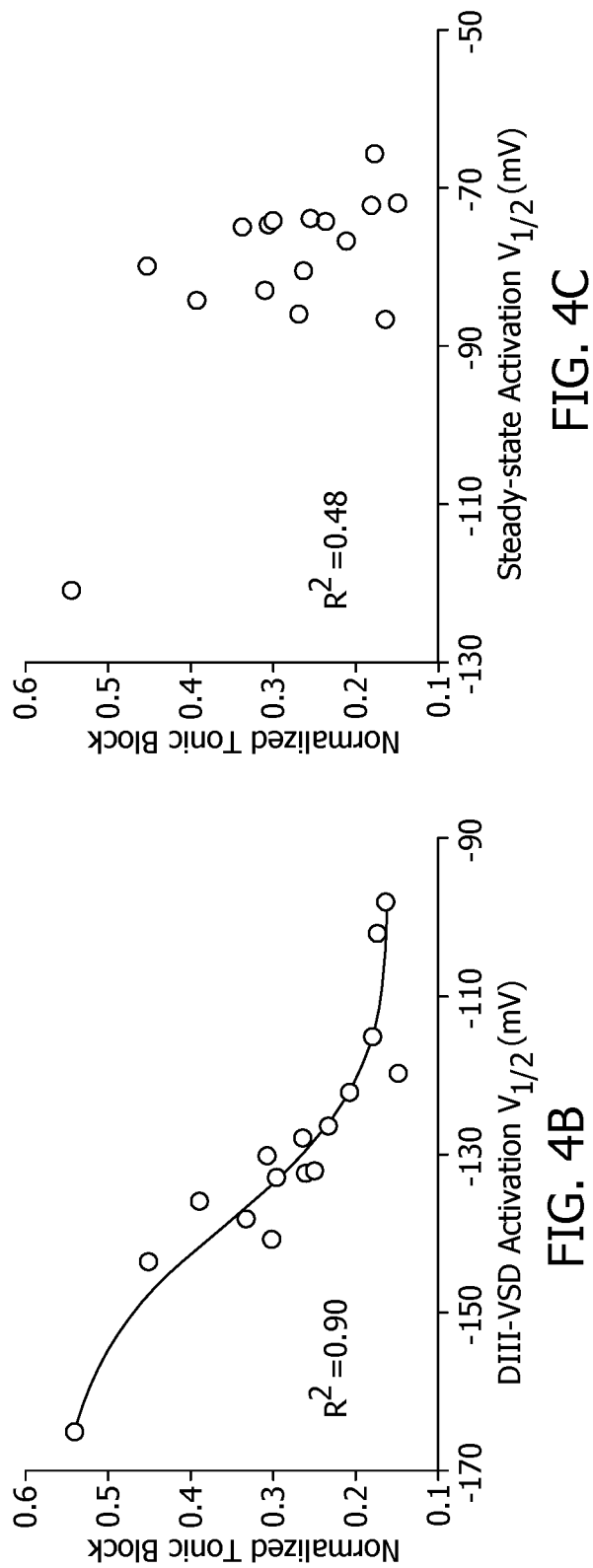
FIG. 4A
FIG. 4B
FIG. 4C

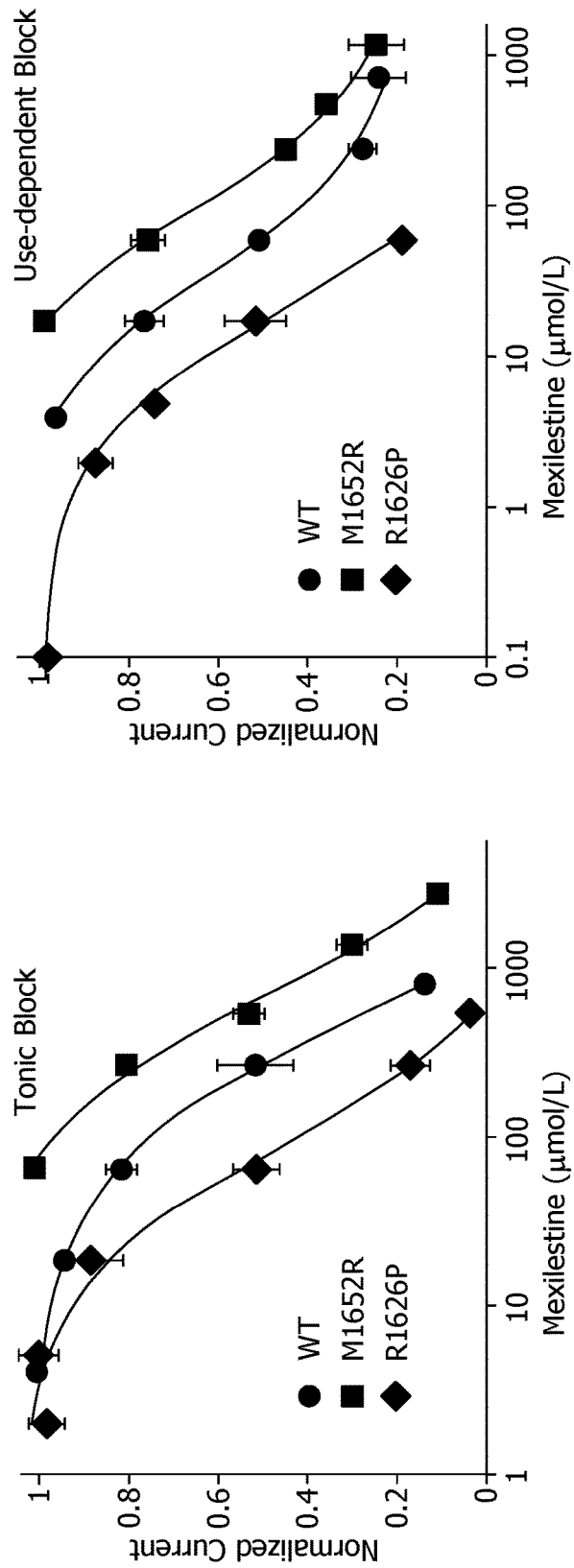
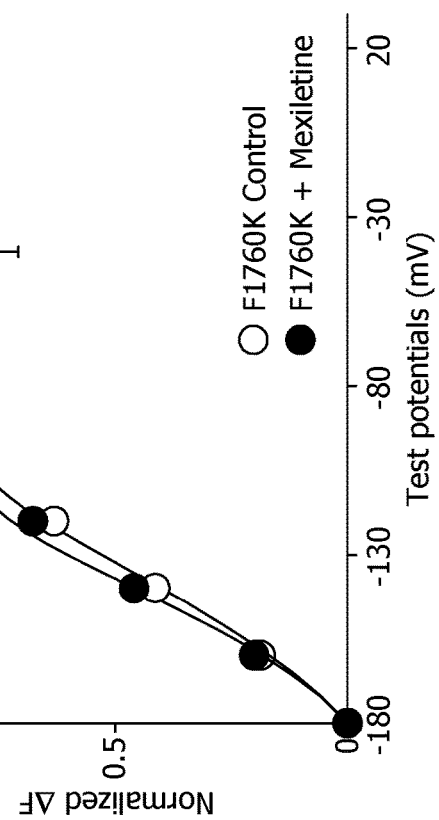
FIG. 8A
FIG. 8B
FIG. 9

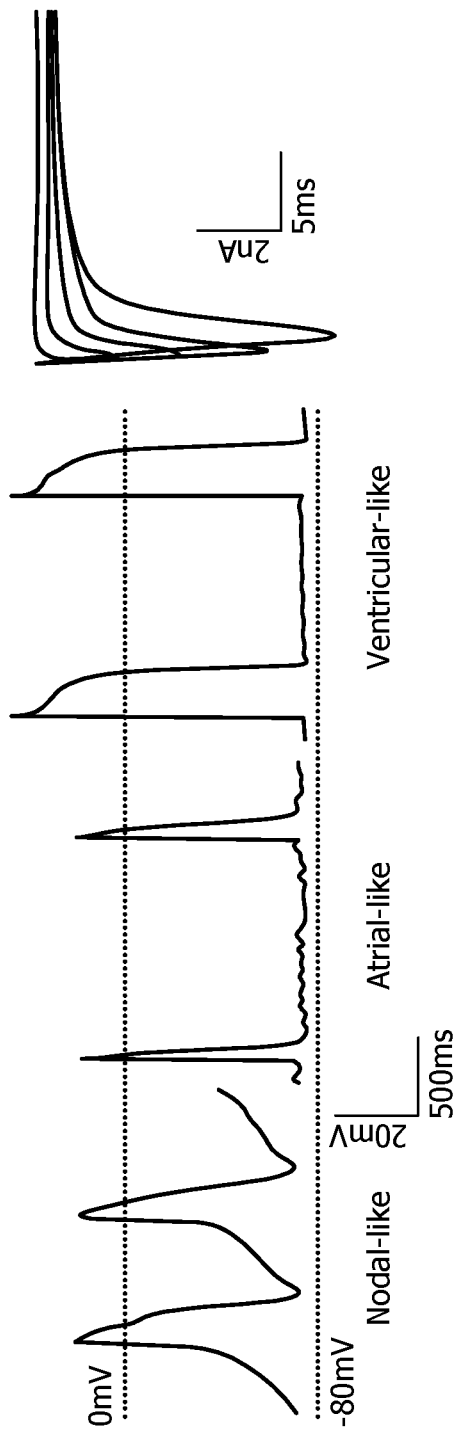
FIG. 19A
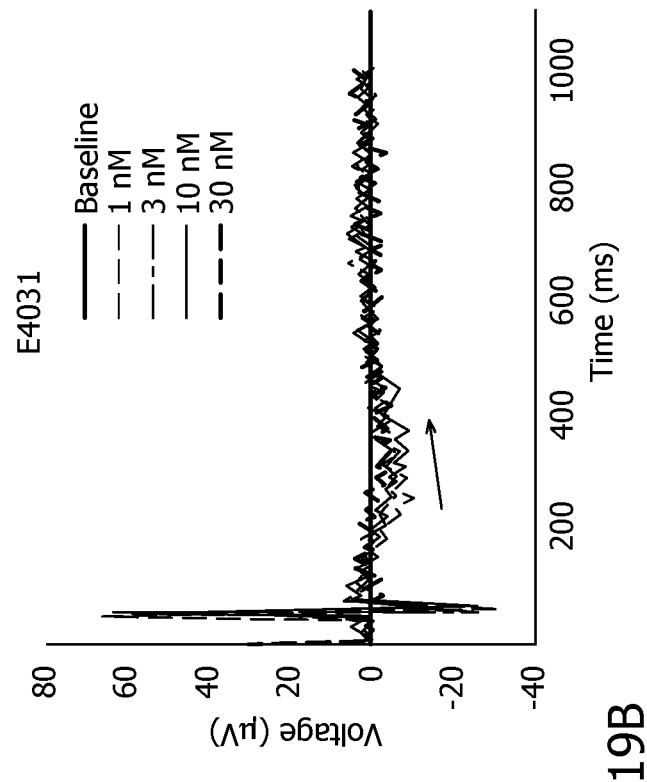
FIG. 19B
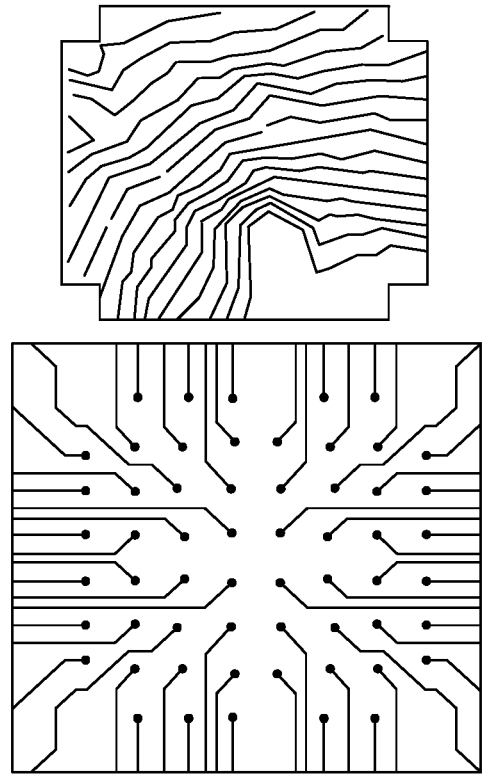

PREDICTING PATIENT RESPONSE TO SODIUM CHANNEL BLOCKERS

STATEMENT REGARDING FEDERALLY SPONSORED RESEARCH & DEVELOPMENT

This invention was made with government support under grant R01HL136553 awarded by the National Institutes of Health. The government has certain rights in the invention.

BACKGROUND

Class Ib antiarrhythmics are widely prescribed to treat patients with ventricular tachycardia, ventricular fibrillation, and Long QT (LQT) syndrome. As a subset of the Class I agents that target the voltage-gated cardiac Na$^+$ channel Na$_V$1.5, Class Ib drugs preferentially inhibit the late component of the Na$^+$ current ($I_{Na}$). Consequently, these drugs shorten action potential duration (APD) and prolong the effective refractory period (ERP), thereby reducing the risk of arrhythmia. Despite Class I agents' common clinical use, these drugs display high variability in efficacy and may cause a pro-arrhythmic response in some patients. For example, the classic Cardiac Arrhythmia Suppression Trial (CAST) showed that patients treated with Na$_V$ channel inhibitors encainide or flecainide (Class Ic) were 2-3 times more likely to experience adverse events than were patients prescribed a placebo. This stunning clinical failure highlights an incomplete understanding of antiarrhythmic therapy and suggests that antiarrhythmic drug action is more complex than currently reflected in the Vaughan-Williams classification scheme that is widely used in clinical practice today.

LQT syndrome is a life-threatening disorder that arises from the inability of the heart to properly repolarize which leads to prolongation of the QT interval on an electrocardiogram. LQT type 3 (LQT3) syndrome is caused by mutations in the SCN5A gene that encodes Na$_V$1.5. The main class of drugs, beta-adrenergic receptor antagonists or partial agonists (beta-blockers), used to treat LQT1 have limited effectiveness for LQT3 patients and may even be proarrhythmic. Consequently, LQT3 is difficult to clinically manage.

Similarly, small molecule drug therapy for ventricular tachycardia (VT) and ventricular fibrillation (VF) has been a longstanding challenge, and large clinical trials have shown that, compared to placebo, antiarrhythmic therapy can paradoxically increase arrhythmia burden and the risk of sudden cardiac death. The subsequent MADIT trials evaluating the efficacy of implantable cardiac defibrillators (ICDs) showed a dramatic reduction in deaths due to arrhythmia and overall mortality. Nevertheless, direct current cardioversion is painful, traumatizing, and can cause post-traumatic stress disorder. In addition, device therapy is not perfect; some patients suffer frequent ICD shocks, while for others, ICD therapy can exacerbate an arrhythmia (e.g. VT degeneration into VF with tachy-therapies). As a result, arrhythmia treatment often relies on the combination of 1) drug therapy to reduce arrhythmia burden, and 2) ICD therapy serving as a safety net for breakthrough arrhythmias.

Amiodarone, a mixed ion channel blocker, is the most commonly prescribed antiarrhythmic drug for patients with ventricular arrhythmias, and multiple trials have shown efficacy. However, patients who receive longterm amiodarone are at risk for serious, potentially fatal, side effects which include liver, pulmonary, ocular, and thyrotoxicity. After 5 years, 70% of amiodarone patients experience at least one adverse effect and after only 1 year, 23% of patients discontinue therapy even at low dose. In contrast to amiodarone, mexiletine, a class 1b Na+ channel blocker, is selective, and does not carry long-term toxicity. However, patient response is variable, and a clinical effect often requires high therapeutic doses, which are limited by mexiletine's side effect profile. Thus, while amiodarone has broad efficacy, it carries broad toxicity. For the right patients, however, mexiletine monotherapy may be a viable option with minimal long-term toxicity.

In recent clinical trials, the orally-available class Ib drug mexiletine effectively shortens QT interval in a subset of LQT3 patients. Despite mexiletine's overall efficacy, a spectrum of QT shortening was observed in patients that carry different SCN5A variants, effects that were reflected in single-cell electrophysiology recordings. A precise understanding of how Na$_V$1.5 mutations alter sensitivity to mexiletine would enable prediction of patient-specific responses and the development of molecularly targeted therapies.

The Na$_V$ channel is a multiprotein complex that contains the α-subunit, which is a monomer that forms the ion-conducting part of the channel. The alpha-subunit has four homologous domains (DI-DIV), each composed by six transmembrane segments, S1-S6. S1-S4 of each domain form the voltage-sensing domain (VSD), and S5-S6 form the pore. Upon cell membrane depolarization, the VSDs activate, the pore opens, and Na$^+$ ions enter the cell. Replacing phenylalanine with lysine at position 1760 in the S6 segment of DIV (DIV-S6) in the Na$_V$1.5 alpha-subunit eliminates UDB by lidocaine, suggesting that the drug binding site is within the pore region of this alpha-subunit. The Na+ selectivity filter, located within the pore, is asymmetric, with each domain contributing a different amino-acid. Similarly, although the four VSDs are homologous, with S4 carrying positive charges that sense Vm, each contributes distinctively to channel function. Specifically, the DI, DII, and DIII VSDs work together to cause channel opening by coupling to the ion-conducting pore through the intracellular S4-S5 linkers. A short stretch of hydrophobic amino acids (I-F-M-T) within the intracellular DIII-DIV linker is essential for inactivation, and has been proposed to directly interact with the DIII and DIV S4-S5 linkers. DIV-VSD activation is rate-limiting for inactivation, and a slower component of DIII-VSD activation stabilizes the inactivated state. Na+ channels comprise large macromolecular complexes with many subunits. The β subunits genes SCN1B-SCN4B each encode a single transmembrane-spanning domain that is tethered to an extracellular Ig-like motif (β1-β4). The β1 and β3 subunits assemble non-covalently with the NaV α subunit (50-52), while the β2 and β4 subunits bind covalently. We have recently demonstrated that the Nav1.5 VSDs are regulated by β1 and β3. In addition to the well-studied transmembrane domains, the intracellular loops of Nav1.5 are vitally important to regulating channel gating and interaction with cell signaling molecules. The DI-DII linker spans 300 amino acids (411-717) and is regulated by numerous post-translational modifications, including phosphorylation at sites that are targeted by protein kinase A (PKA) and sites targeted by Ca2+/calmodulin-dependent protein kinase II (CaMKII). Furthermore, 14-3-3 binding to the DI-DII linker enables Nav1.5 to assemble and gate as a dimer. The DII-DIII linker contains 267 amino acids (939-1206) and interacts with MOG1 and Ankyrin-G. A splice-variant Nav1.5-δ lacks 40 amino acids from the DII-DIII linker, resulting in significant changes to activation and inactivation that reduce current amplitude.

Binding of local anesthetics to $Na_V1.5$ also modulates the VSDs. The pore and VSDs are tightly coupled; therefore, conformational changes induced by the binding of drugs within the pore can affect the voltage and time dependence of VSD conformation. Experiments that monitor VSD activation show that lidocaine binding stabilizes an activated conformation of VSD of DIII (DIII-VSD). This phenomenon is thought to be caused by lidocaine holding the pore-forming S6 of DIII (DIII-S6) in a partially open conformation even under hyperpolarized potentials, which then allosterically modulates the DIII-VSD stabilizing the activated conformation. Lidocaine is a prototypical anti-arrhythmic molecule. Most class I therapies, defined by their block of Nav1.5, resemble its structure. Differences in how drugs enter the channel result in various action potential phenotypes that lead to subclassification into class 1a, 1b and 1c, where 1b molecules maximize block of persistent Na+ current, while minimizing the impact on peak current and impulse propagation. While lidocaine is an effective anti-arrhythmic drug, 70% of molecules in the bloodstream undergo first-pass hepatic metabolism. Mexiletine was developed as an oral analogue of lidocaine, with a very similar structure, that is not as easily metabolized by the liver (<10% first pass) and has much greater bioavailability when taken orally. Nevertheless, early trials demonstrated that only a subset of patients had reduced arrhythmia burden.

Large genetic studies have provided critical insight into the regulators of the human heartbeat and variants that predispose patients to arrhythmia. However, these approaches cannot be used to discover how variants will respond to drug therapy, due to the impossibility of recruiting enough patients to connect a given variant to a drug response.

Previous work has also correlated the kinetics of Nav channel activation and inactivation to use-dependent and tonic block. These approaches have been of limited utility in predicting patient response to anti-arrhythmic drugs, because both activation and inactivation involve many different transitions within the channel, with only a few correlating with drug block.

Thus, there is a need to determine the mechanism by which different sodium ion channel blockers block $Na_V1.5$ channels and the heterogeneous response to sodium ion channel blockers of different LQT3 variants. Additionally, there is a need to predict patient response to sodium ion channel blockers based on channel molecular gating properties in order to improve patient therapy and outcomes.

More specifically, there is a need to determine the mechanism by which mexiletine blocks $Na_V1.5$ channels and the heterogeneous response to mexiletine of different LQT3 variants. Additionally, there is a need to predict patient response to mexiletine therapy based on channel molecular gating properties in order to improve patient therapy and outcomes.

There is also a need to determine how genetic variation and β-adrenergic tone impact mexiletine interaction with Nav 1.5, including in patients with ventricular arrhythmias. What is further needed is this knowledge combined with the increasing availability of low-cost sequencing and heart rhythm reports from wearable and implanted devices. What is further needed is optimized drug and device therapy for a particular patient based on variables including their genetic variation, β-adrenergic tone, or both, in order to decrease the risk of deadly rhythm disturbance. What is still further needed is a predictive model that comprises at least one and preferably more than one of the variables. What is still further needed is a predictive model that maps parameters associated with the variables and patient response. What is further needed are methods for improving the predictive model by gaining insight from an optimized induced pluripotent stem cell based model of the drug response. Finally what is needed is a clinical trial that uses a predictive model to identify ventricular arrhythmia patients who will respond to mexiletine based on data that is becoming readily available to physicians.

What is further needed is to use biophysical insight into the structural regulators of the Nav1.5-mexiletine interaction to define key parameters responsible for mexiletine's efficacy.

What is further needed is a method that removes the need to recruit large numbers of each variant and to construct a predictive model by mapping variants to these parameters.

What is still further needed is an application of all of the above approaches for predicting how patients who suffer from VT/VF will respond to sodium ion channel blockers such as mexiletine.

What is further needed are novel approaches to match patients to arrhythmia treatment and to reveal the function of intrinsically disordered loops in ion channels.

BRIEF DESCRIPTION

Disclosed herein is a method for predicting a patient response to a sodium ion channel blocker when the patient has LQT syndrome. The method generally comprises determining a plurality of parameters associated with sodium ion channels; generating a model for patient response by using a partial least squared (PLS) regression analysis on said plurality of parameters; and using the model to predict the patient response if the patient is administered the sodium ion channel blocker.

Also disclosed herein is an in vitro method for predicting a patient response to a sodium ion channel blocker when the patient has LQT syndrome. The method generally comprises: collecting a biological sample from the patient; expressing at least one gene from the biological sample; testing the expressed gene for a plurality of parameters; and using the plurality of parameters in a model to predict the patient response to the sodium ion channel blocker.

Also disclosed herein is a method for predicting a patient response to a sodium ion channel blocker when the patient has an arrhythmia such as ventricular tachycardia (VT) and ventricular fibrillation (VF). The method generally comprises determining a plurality of parameters associated with sodium ion channels; generating a model for patient response by using a partial least squared (PLS) regression analysis on said plurality of parameters; and using the model to predict the patient response if the patient is administered the sodium ion channel blocker.

Also disclosed herein is an in vitro method for predicting a patient response to a sodium ion channel blocker when the patient has an arrhythmia ventricular tachycardia (VT) and ventricular fibrillation (VF) syndrome. The method generally comprises: collecting a biological sample from the patient; expressing at least one gene from the biological sample; testing the expressed gene for a plurality of parameters; and using the plurality of parameters in a model to predict the patient response to the sodium ion channel blocker.

In some forms, the methods of the disclosure will not rely solely on Na+ channel conductance measurements to study channel-drug interactions. Instead, tethered fluorophores, called voltage-clamp fluorometry (VCF), will be used to track the conformations of individual Nav channel domains.

From these data, we developed models that predicted the pharmacokinetics of class Ib molecules with greater accuracy than could be achieved with models that only account for use-dependent and tonic block.

In some forms, the methods of the disclosure will evaluate the phosphorylation state of the channel and VSD dynamics of additional Nav variants to develop methods and models that predict patient response to anti-arrhythmic drugs based on Nav genetics.

In some forms of the disclosure, channel physiology will be connected to the conformational dynamics of intrinsically disordered loops. In cardiac Nav channels, the intracellular loops are intrinsically disordered. Thus, accurately predicting whether a given variant within these loops will affect channel gating and understanding the mechanisms involved has not been possible. Recent theoretical advances enabled the simulation of huntingtin, tau, and Aβ peptides to improve understanding of how genetic variants alter their conformational dynamics. These methods are applied to study how molecular movements of the intrinsically disordered Nav1.5 loops influence channel function.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Unless otherwise indicated, the drawings and figures provided herein illustrate features of embodiments of the disclosure or results of representative experiments illustrating some aspects of the subject matter disclosed herein. These features and/or results are believed to be applicable in a wide variety of systems including one or more embodiments of the disclosure. As such, the drawings are not intended to include all additional features known by those of ordinary skill in the art to be required for the practice of the embodiments, nor are they intended to be limiting as to possible uses of the methods disclosed herein.

FIG. 1A depicts representative current traces before and after 250 µM mexiletine tonic block (TB) and use-dependent block (UDB). Comparison between traces before and after mexiletine shows that mexiletine reduces the peak current by 10.5%, but the later component (10 ms after peak) by 31.5%.

FIG. 1B depicts the steady-state inactivation (SSI) curves before (control, open circles) and after (mexiletine, closed circles) 2 mM mexiletine. Channel SSI was tested by holding the cells from −150 to 20 mV with a 10 mV increment for 200 ms. Fraction of channels available were then measure by peak currents induced by a −20 mV test pulse. Mexiletine induces minimal hyperpolarizing shift in SSI curve.

FIG. 1C is a graph illustrating the channel recovery from inactivation curves before (control, open circles), and after (mexiletine, closed circles) 250 uM mexiletine. Cells were first depolarized to −20 mV to induce inactivation, then allowed to recover at −120 mV for various durations. Fraction of channels recovered were then tested with a −20 mV pulse. Mexiletine slows down both phases of recovery, especially the slow recovery.

FIG. 2A illustrates the topology of $Na_v1.5$ channel and location of the two LQT mutations with distinct mexiletine sensitivity, R1626P (red ball, sensitive) and M1652R (green ball, insensitive).

FIG. 2B depicts the concentration dependence of tonic block (TB) by mexiletine for WT, R1626P, and M1652R channels expressed in Xenopus oocytes. $EC_{50}$ values were 760.8 µM for WT, 2035.3 µM for M1652R, and 211.1 µM for R1626P channels.

FIG. 2C depicts the concentration dependence of use-dependent block (UDB) by mexiletine. Currents were normalized to the peak current elicited by the first depolarizing pulse. EC50 values were 58.4 µM for WT, 192.7 µM for M1652R, and 56.6 µM for R1626P channels.

FIG. 2G depicts a proposed schematic showing possible mechanisms underlying the difference in mexiletine sensitivities between R1626P and M1652R. The DIII-VSD in the upward position represents the activated conformation. The lower position represents the inactivated conformation. At resting potential, R1626P has more activated DIII-VSD, which is coupled to the DIII pore domain (S5, S6), causing the pore to remain in a conformation with increase accessibility for mexiletine. In contrast, insensitive M1652R fewer activated DIII-VSDs, causing the DIII-pore to enter a conformation with less accessibility.

FIG. 2H illustrates the relationships between % of block and the fraction of DIII-VSD activated, or the fraction of current available for four different holding potentials (−120, −110, −100, −90 mV). The fraction of current availability for four potentials are not significantly different from each other. The fraction of the DIII-VSD activated shows a linear relationship with the % of TB.

FIG. 2I depicts the TB by 500 µM mexiletine for F1760K, R1626P F1760K, M1652R F1760K channels. TBs are not significantly different, suggesting that the F1760K eliminates LQT variant-dependent mexiletine sensitivity.

FIG. 3A illustrates locations of the decoupling mutation A1326W and two LQT3 variant mutations, R1626P and M1652R. A1326W resides on the S4-S5 linker of DIII, a motif that is known to regulate energetic coupling between the VSD and pore.

FIG. 3B depicts the concentration dependence of TB for A1326W, M1652R-A1326W, and R1626P-A1326W channels. EC50 values were 965.2 µM for WT, 1562.3 µM for M1652R, and 1440.7 µM for R1626P channels.

FIG. 3C depicts the concentration dependence of UDB for M1652R-A1326W, and R1626P-A1326W channels. EC50 values were 113.0 μM for WT, 51.2 μM for M1652R, and 51.6 μM for R1626P channels.

FIG. 3D depicts the voltage dependence of steady-state fluorescence of DIII for A1326W, M1652R-A1326W, and R1626P-A1326W channels. The differences in voltage dependence of DIII-VSD activation is similar with the A1326W as a background mutation. DIII F-V curve of M1652R-A1326W still showed depolarizing shift, while R1626P-A1326W showed hyperpolarizing shift compared to A1326W channels.

FIG. 3E depicts the steady-state inactivation (SSI) curves of WT, R1626P, and M1652R channels. The differences in SSI among different mutations are also preserved in presence of the A1326W background mutation.

FIG. 3F illustrates a proposed schematic showing a model of how A1326W eliminates the different sensitivities among LQT variants.

FIG. 4A illustrates that the voltage dependence of DIII-VSD activation strongly correlates with tonic block by mexiletine. It depicts the locations along the primary sequence and channel topology of 15 LQT3 variants tested.

FIG. 4B illustrates the relationship between the voltage dependence of DIII-VSD activation ($V_{1/2}$ of DIII F-V) and normalized tonic block by mexiletine. The data were fitted with a Boltzmann function and the correlation calculated. A strong correlation (R2=0.9) between these two parameters were observed when fitted with a Boltzmann function.

FIG. 4C illustrates the relationship between the SSI ($V_{1/2}$ of SSI) and normalized tonic block by mexiletine. The two parameters are not well-correlated, suggesting that channel inactivation is not a good predictor of mexiletine tonic block.

Figure 5A:
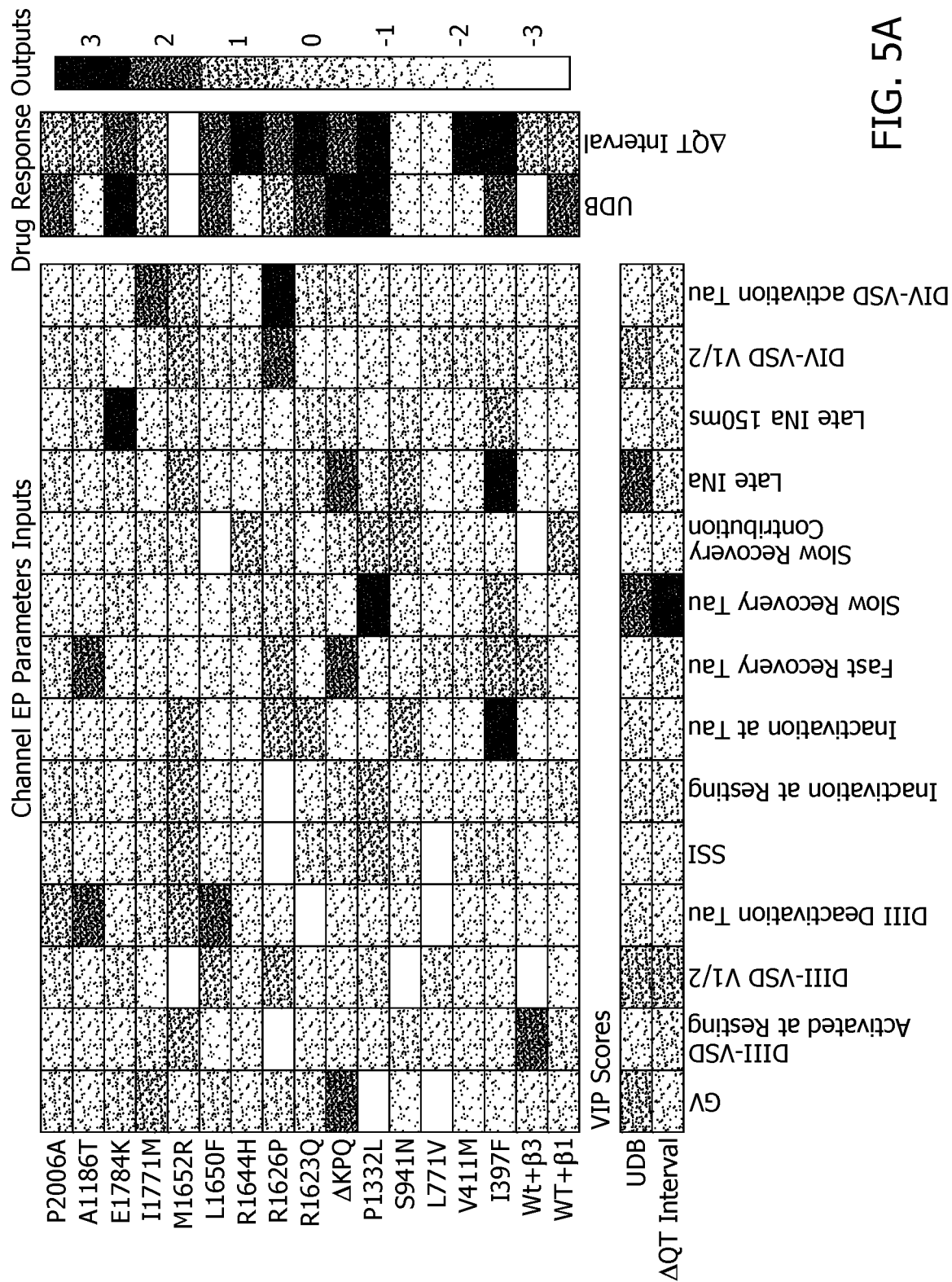

FIG. 5A illustrates (Left side) a heatmap of 14 quantified electrophysiological parameters (EP) of the gating for 15 LQT3 variants and WT channels with β1 or β3 subunits; (Right ride) a heatmap of each channel's responses to mexiletine, including UDB and QTc shortening (ΔQTc) in LQT3 patients undergoing mexiletine treatment; (Bottom) VIP scores for each gating parameter. VIP scores were ranked by each parameter's impact on model fitness. Each gating parameter is removed individually, and PLSR model was constructed with the rest of parameters. The corresponding model fitness was calculated based on Pearson correlation between measured block and predicted block with leave-one-out cross-validation. Higher VIP score (red) suggests that the gating parameter is more important for improving the model fitness.

Figure 5C:
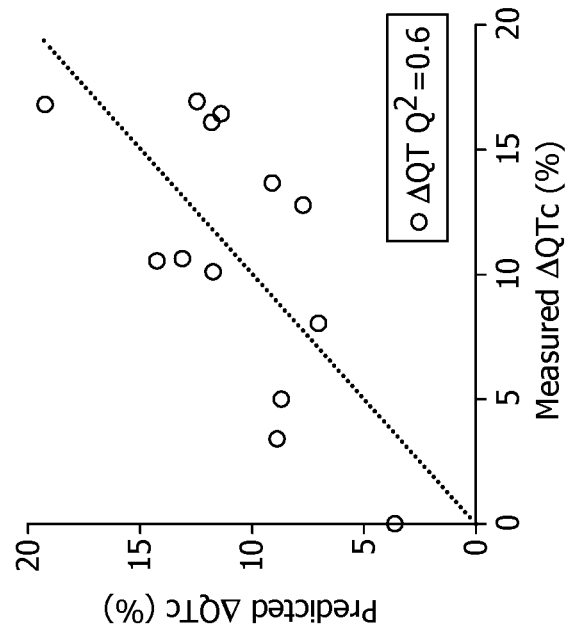
Figure 5B:
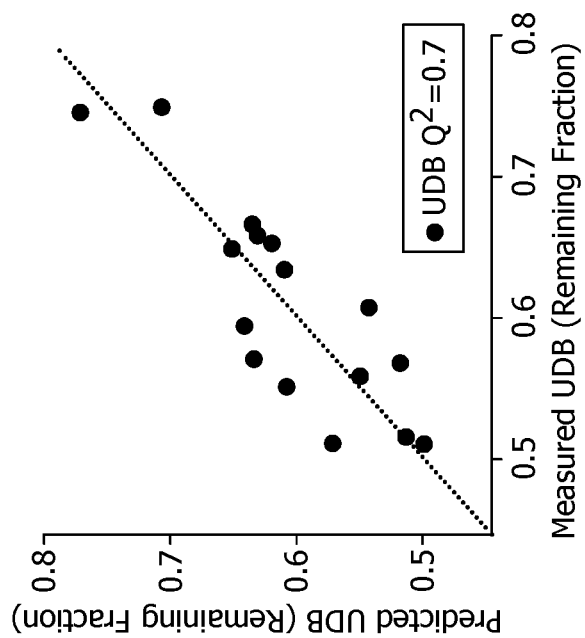

FIG. 5B illustrated the relationship between measured and predicted UDB or ΔQTc. The predictions were made using the PLS regression model with parameters with high VIP scores. Model stability was tested with leave-one-out cross validation.

FIG. 5C illustrates the relationship between measured and predicted ΔQTc. The predictions were made using the PLS regression model with parameters with high VIP scores. Model stability was tested with leave-one-out cross validation.

Figure 6A:
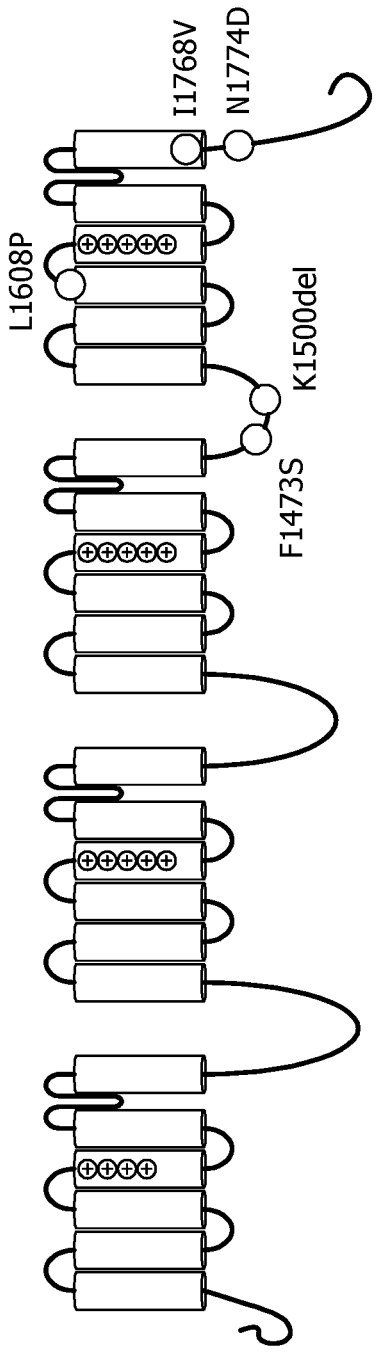

FIG. 6A illustrates the locations of 5 LQT3 variants that are included in the clinical trial and were not used for training the model.

Figure 6B:
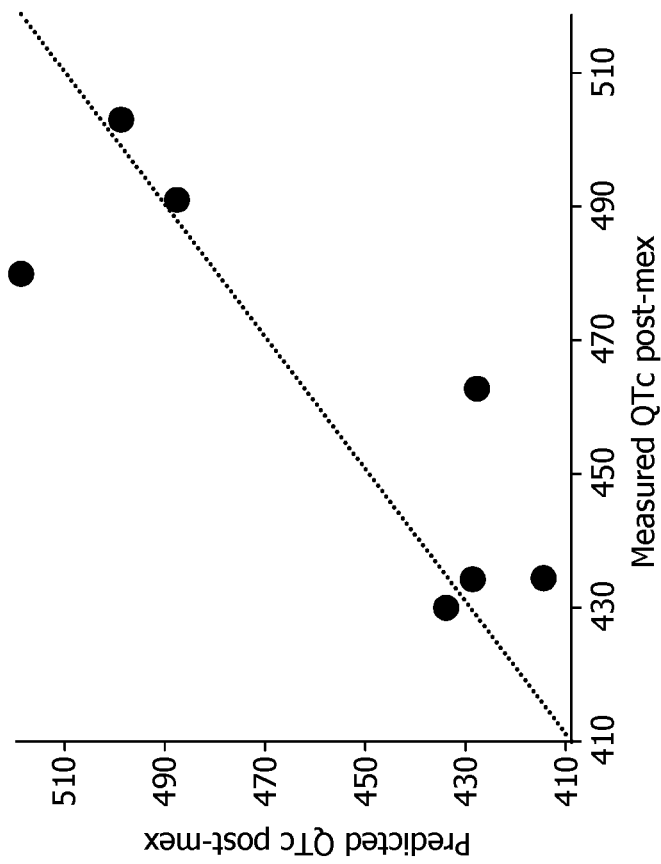

FIG. 6B illustrates a comparison of the measured patients' QTc after mexiletine therapy and the predicted QTc after mexiletine using the PLS regression model.

Figure 7:
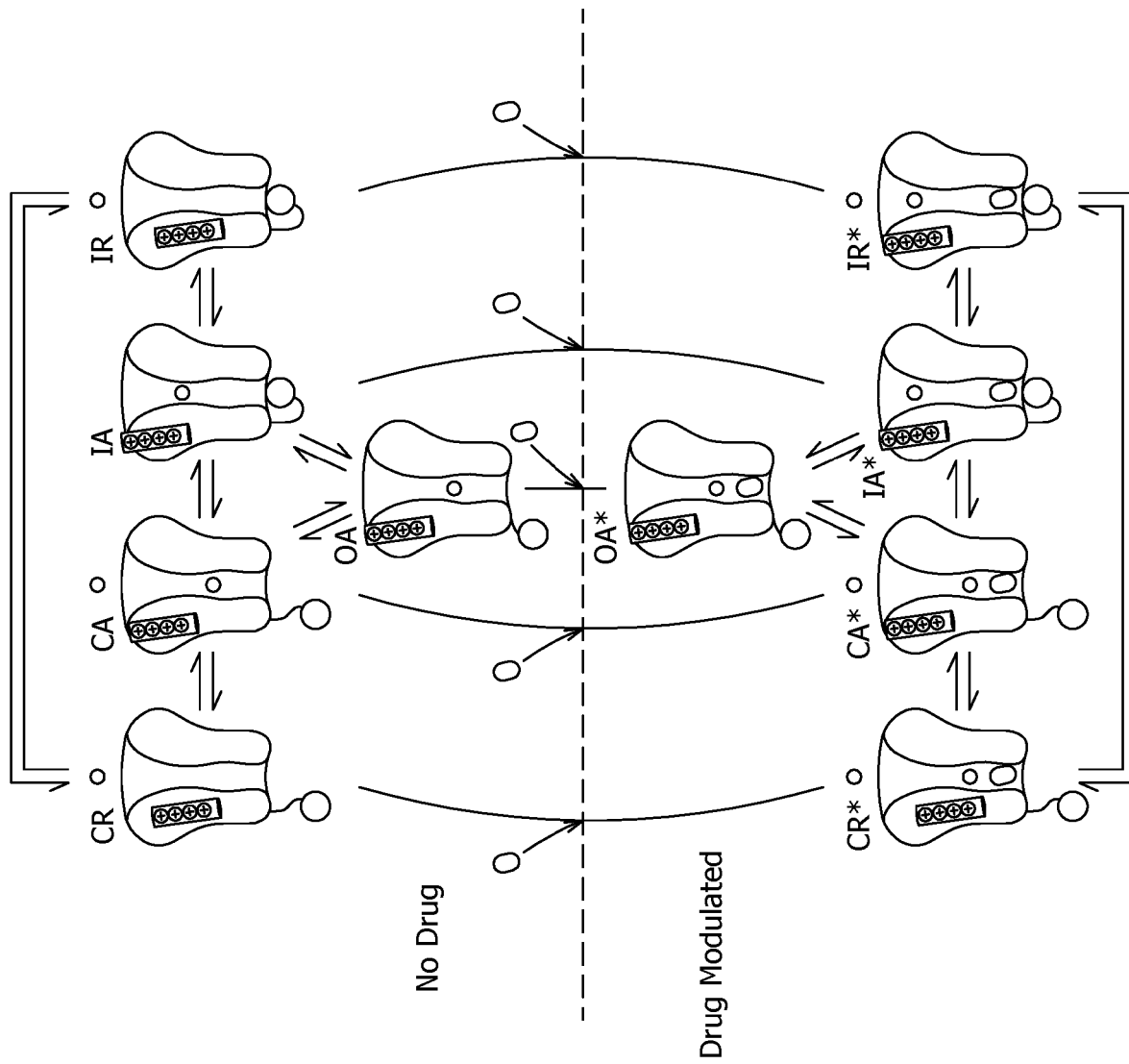

FIG. 7 illustrates the proposed updated modulated receptor model for class Ib antiarrhythmics.

FIG. 8A illustrates the mexiletine dose response curves for WT, M1652R and R1626P channels tested in oocytes with TEVC set-up.

FIG. 8B illustrates the mexiletine dose response curves for WT, M1652R and R1626P channels tested in oocytes with TEVC set-up.

FIG. 9 depicts the DIII F-V curves for F1760K channel before and after mexiletine blockade. Mexiletine no longer affects the voltage-dependence of the DIII-VSD in present of the F1760K mutation.

Figure 10A:
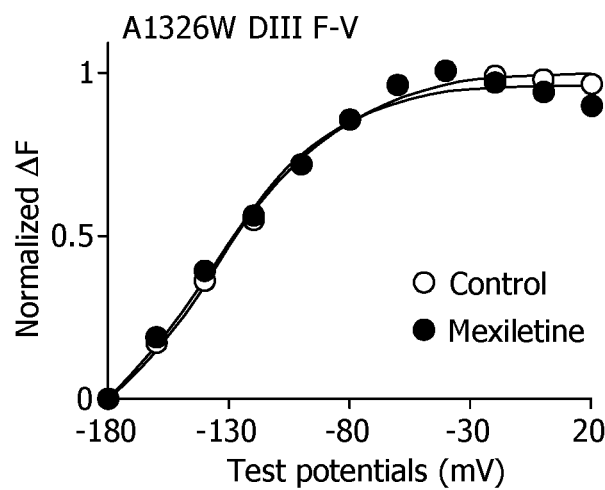
Figure 10A:
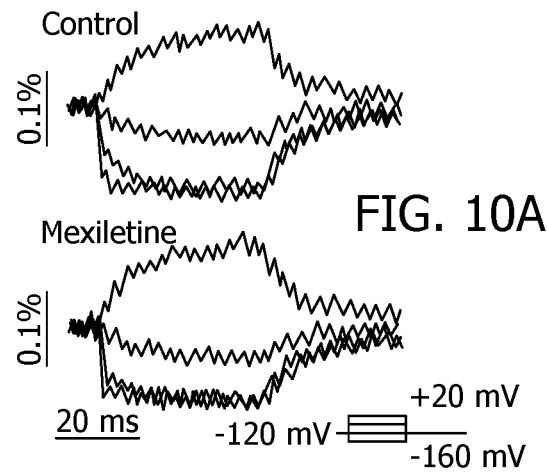
Figure 10B:
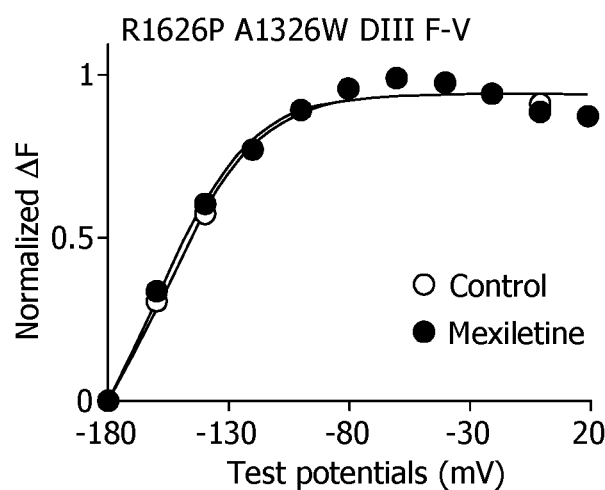
Figure 10B:
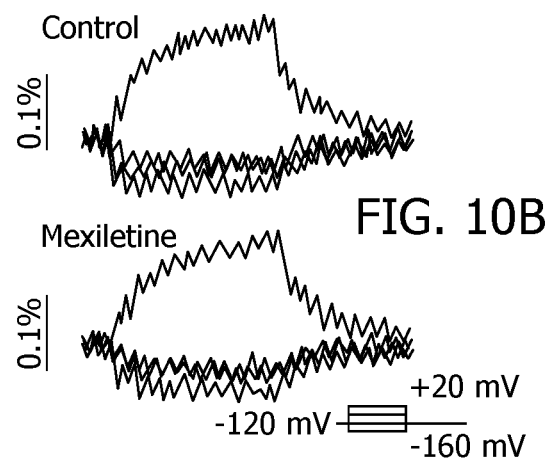
Figure 10C:
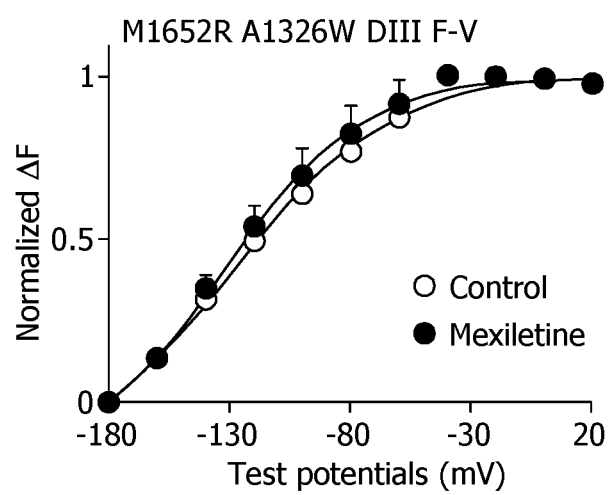
Figure 10C:
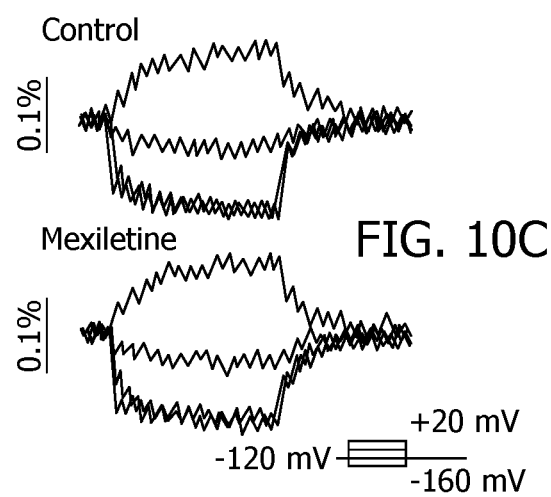

FIG. 10A depicts the DIII F-V curves for A1326W before and after mexiletine binding;

FIG. 10B depicts the DIII F-V curves for R1626P A1326W before and after mexiletine binding;

FIG. 10C depicts the DIII F-V curves for M1652R A1326W channels before and after mexiletine binding. When the DIII-VSD is decoupled from the pore by A1326W mutation, mexiletine blockade of the pore no longer affects the DIII-VSD.

Figure 11A:
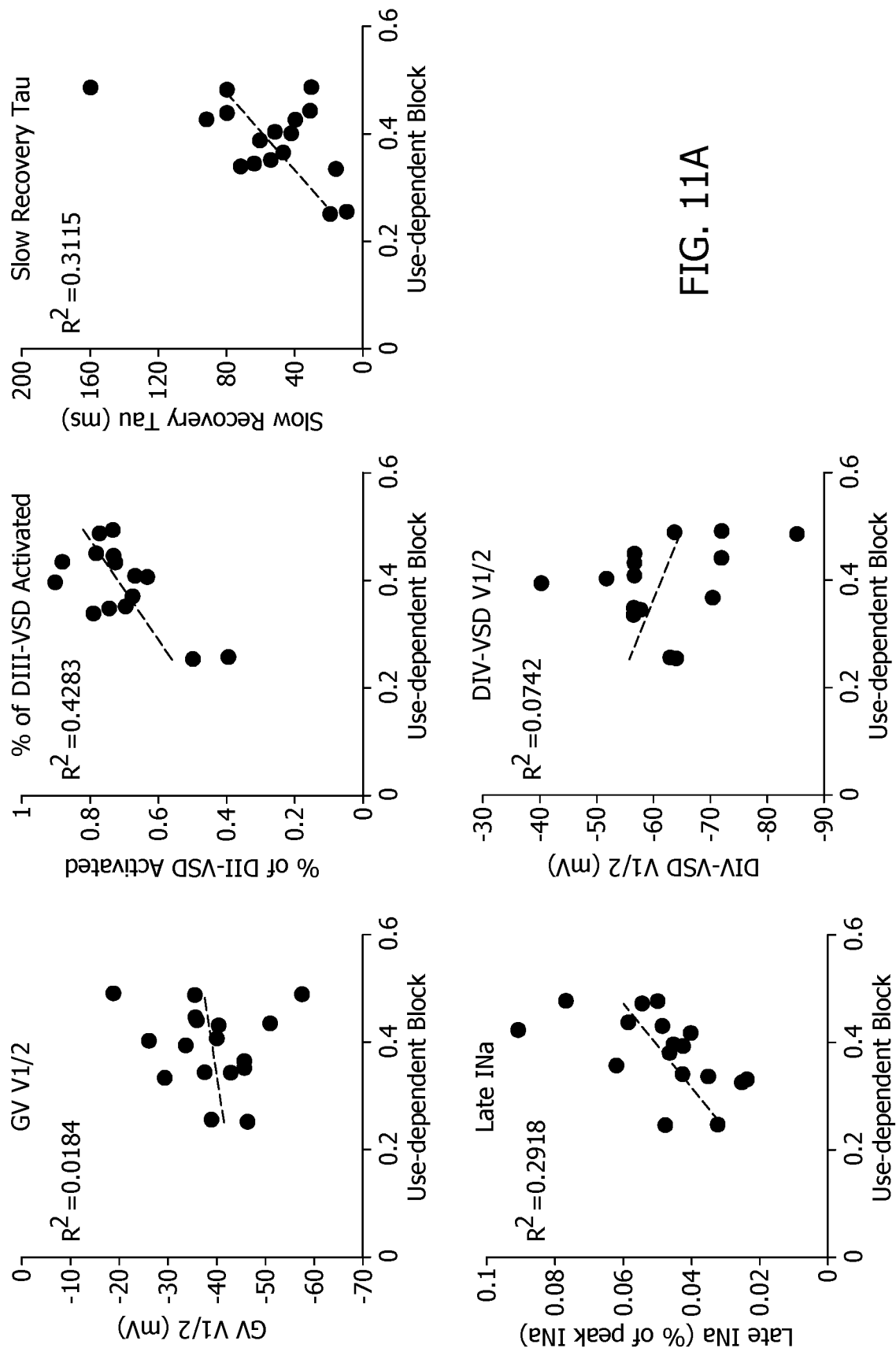
Figure 11B:
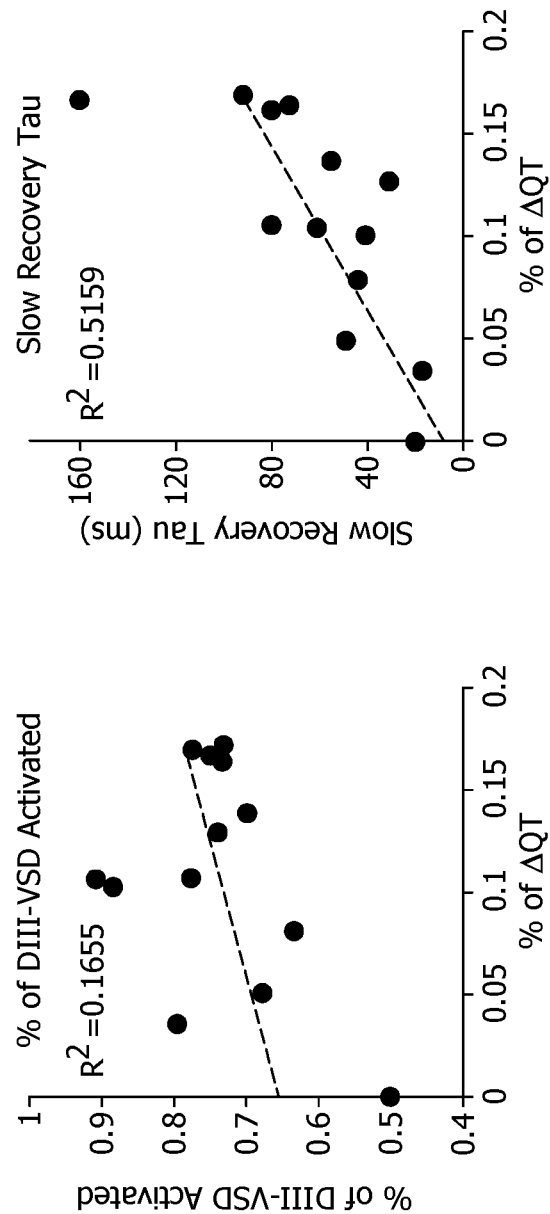

FIG. 11A illustrate the relationships between mexiletine use-dependent block (UDB) and 5 different gating parameters;

FIG. 11B illustrates the relationships between QT shortening by mexiletine in patients (% of ΔQT) and 2 different gating parameters. There is no clear correlation between single gating parameter and ΔQT or UDB.

Figures 12A, 12B:
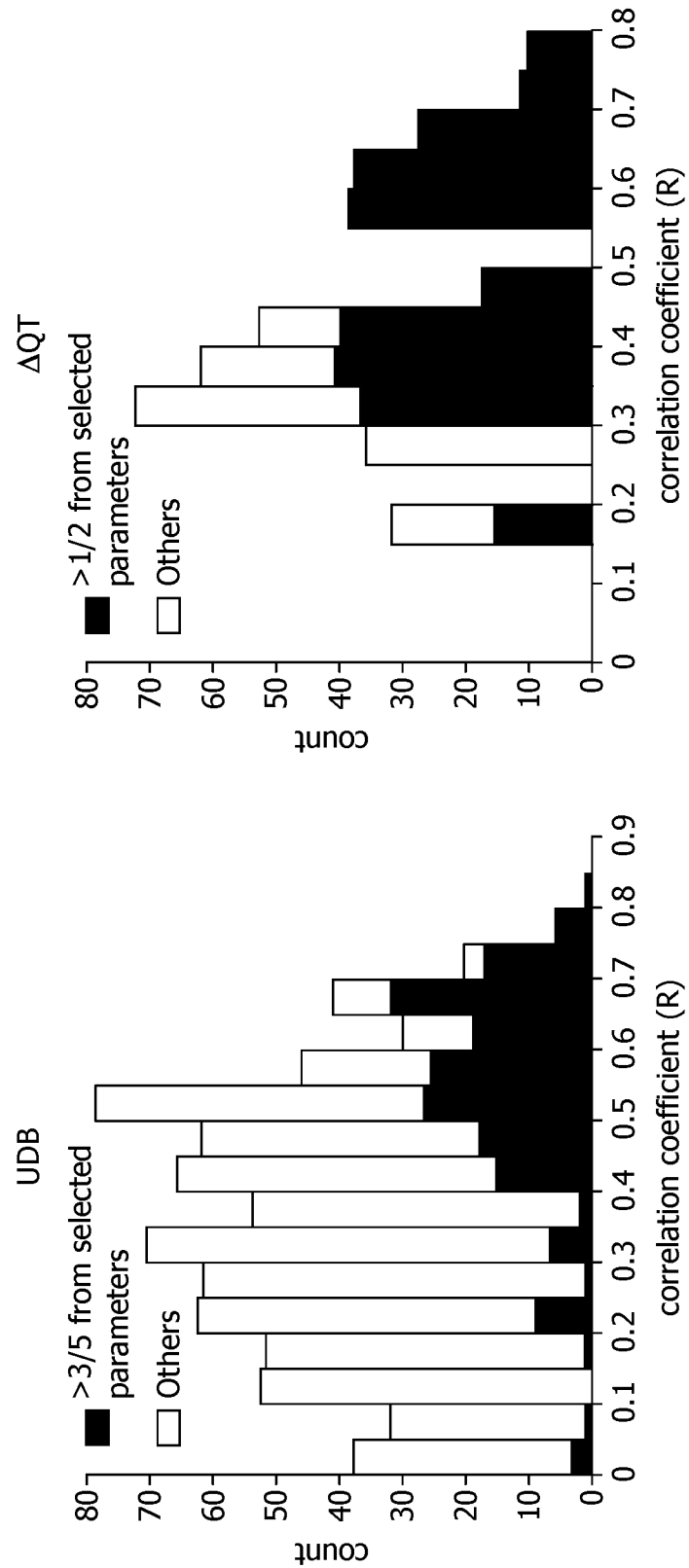

FIG. 12A is a histogram of model fitness (R) for predicting UDB of 1000 PLSR models with 5 random selected parameters (blue) respectively. The fraction of models that contains 3 out of 5 (UDB) parameters with high VIP scores are shown in red. Those models have higher fitness than the rest of models, suggesting parameter selection based on VIP scores increases the model prediction accuracy.

FIG. 12B is a histogram of model fitness (R) for predicting ΔQT of 1000 PLSR models with 2 random selected parameters (blue) respectively. The fraction of models that contains 1 out of 2 (ΔQT) parameters with high VIP scores are shown in red. Those models have higher fitness than the rest of models, suggesting parameter selection based on VIP scores increases the model prediction accuracy.

Figure 13:
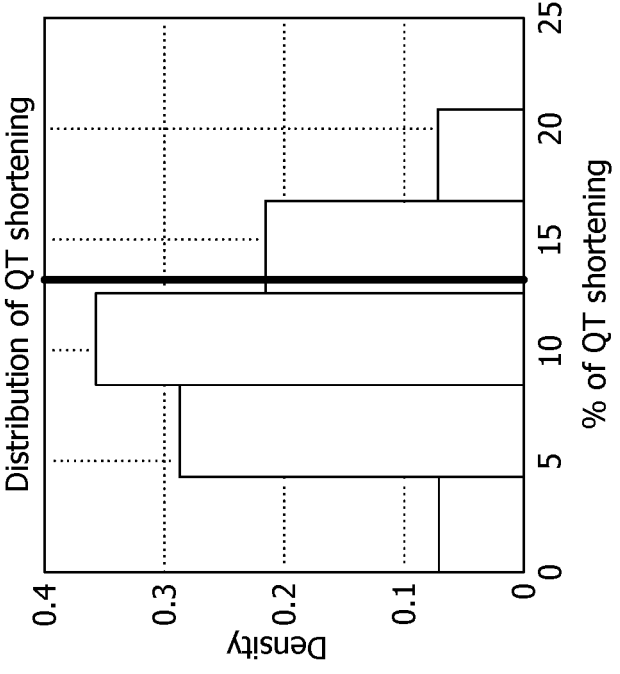

FIG. 13 illustrated the mexiletine QTc calculator: user-interface for the PLS regression model.

Figure 14:
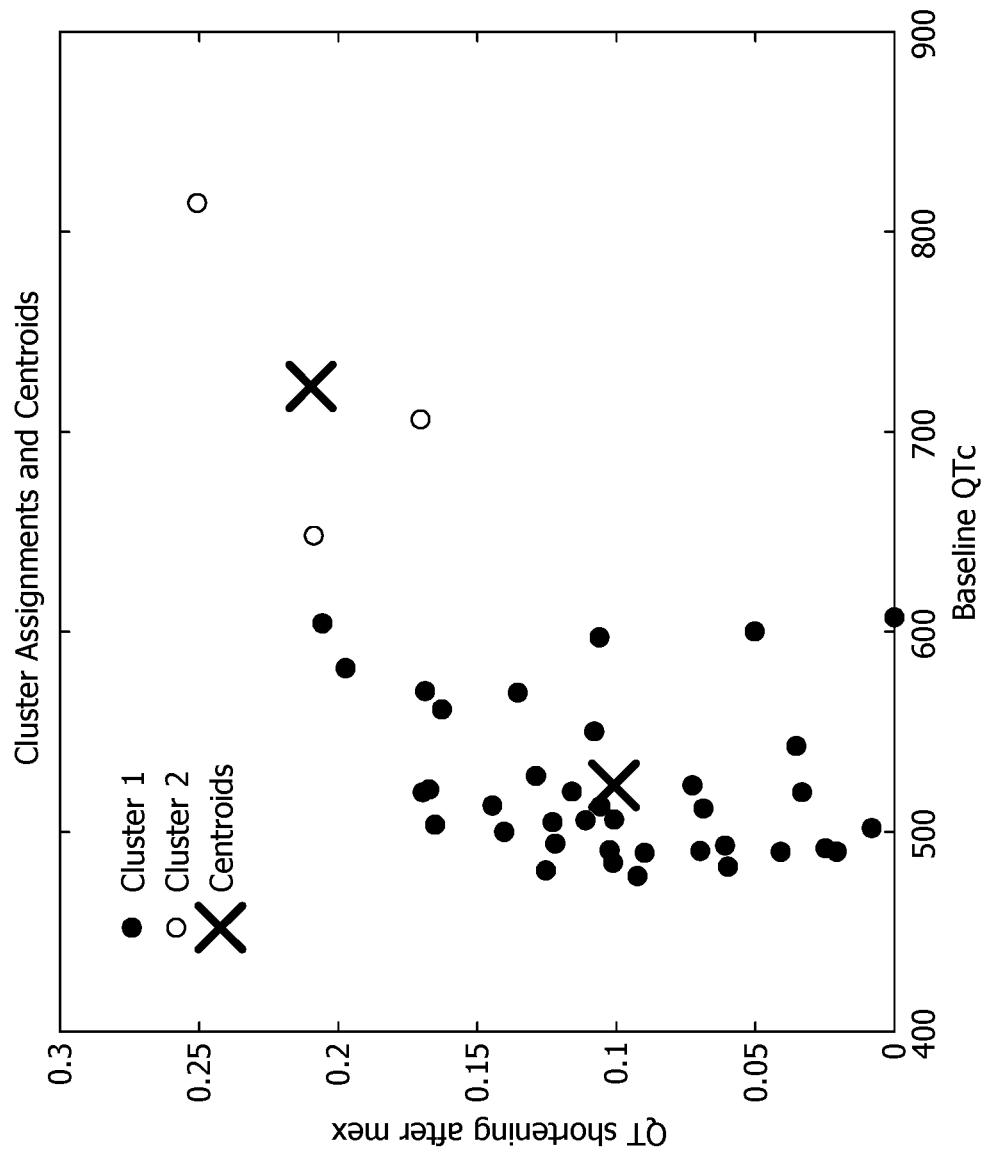

FIG. 14 depicts the relationship between patients' baseline QTc and QTc shortening by mexiletine.

Figure 15:
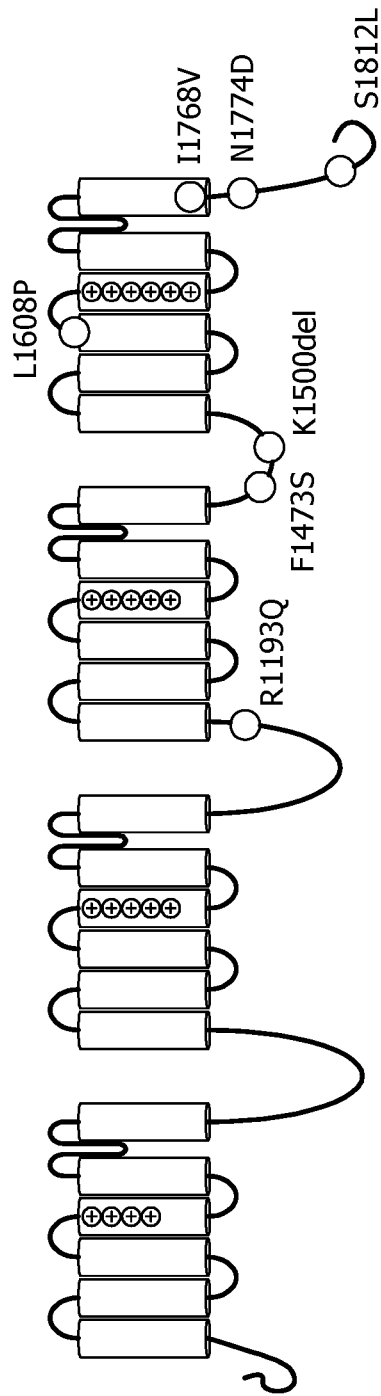
Figure 15:
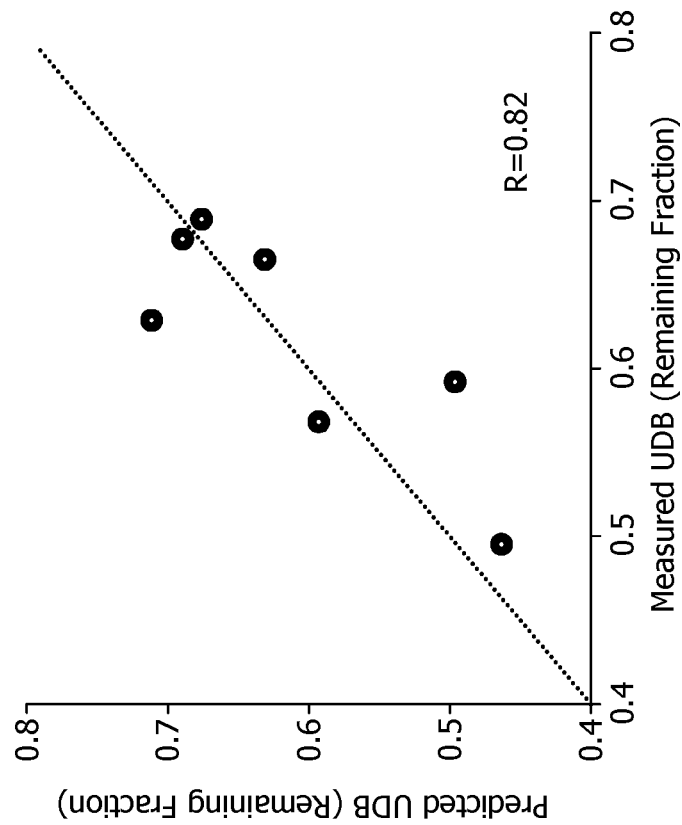

FIG. 15 depicts the predicted UDB for 7 new test variants with the PLS model.

Figure 16:
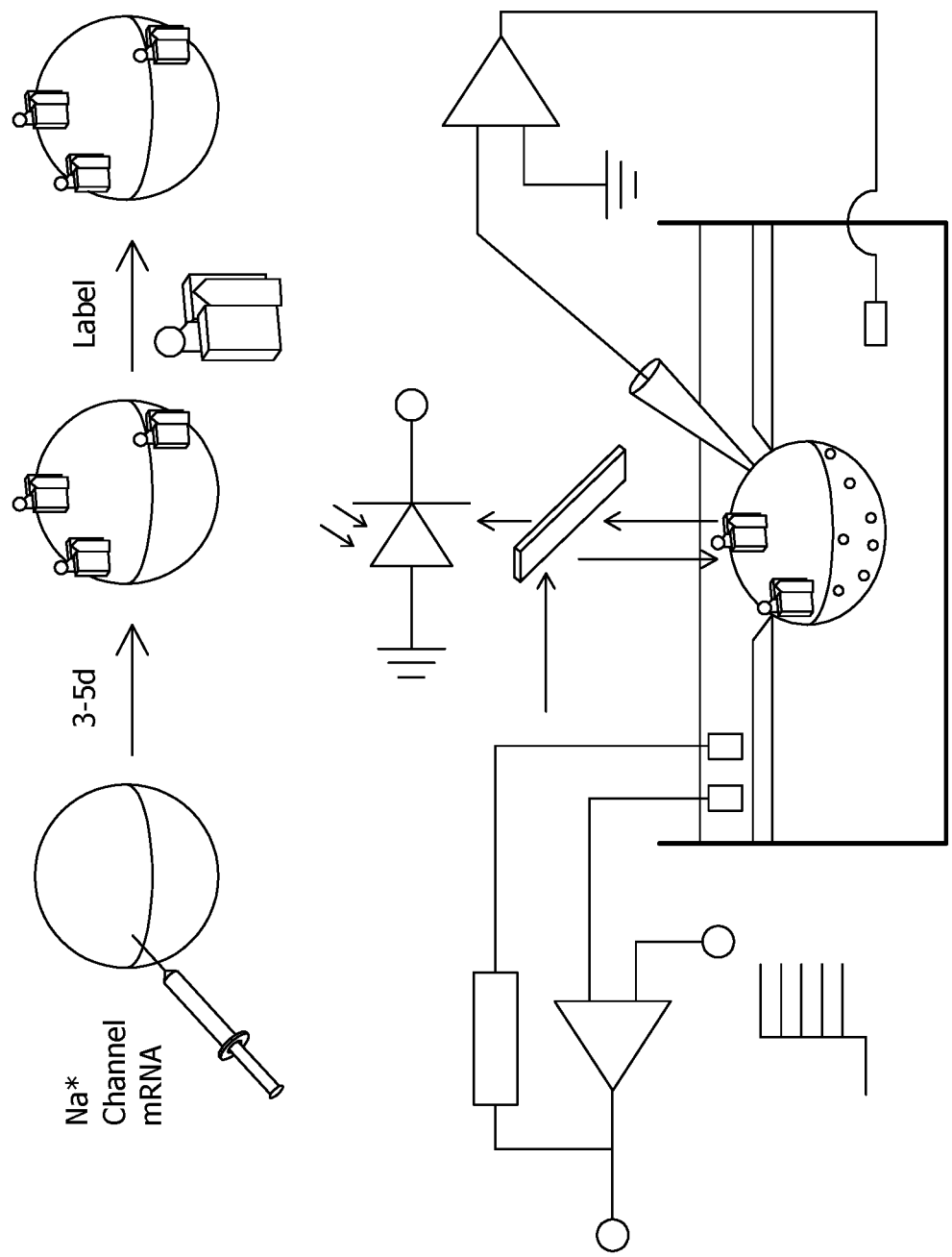

FIG. 16 is a schematic representation of *Xenopus* oocytes being injected with mRNA, and expressing NaV1.5 at high levels after several days. Cysteines are then labeled with a fluorophore. The lower schematic representation illustrates a cut-open oocyte ionic current recording for resolving fast kinetics by clamping a small membrane patch and using a photodiode to collect fluorescence emission.

Figure 17A:
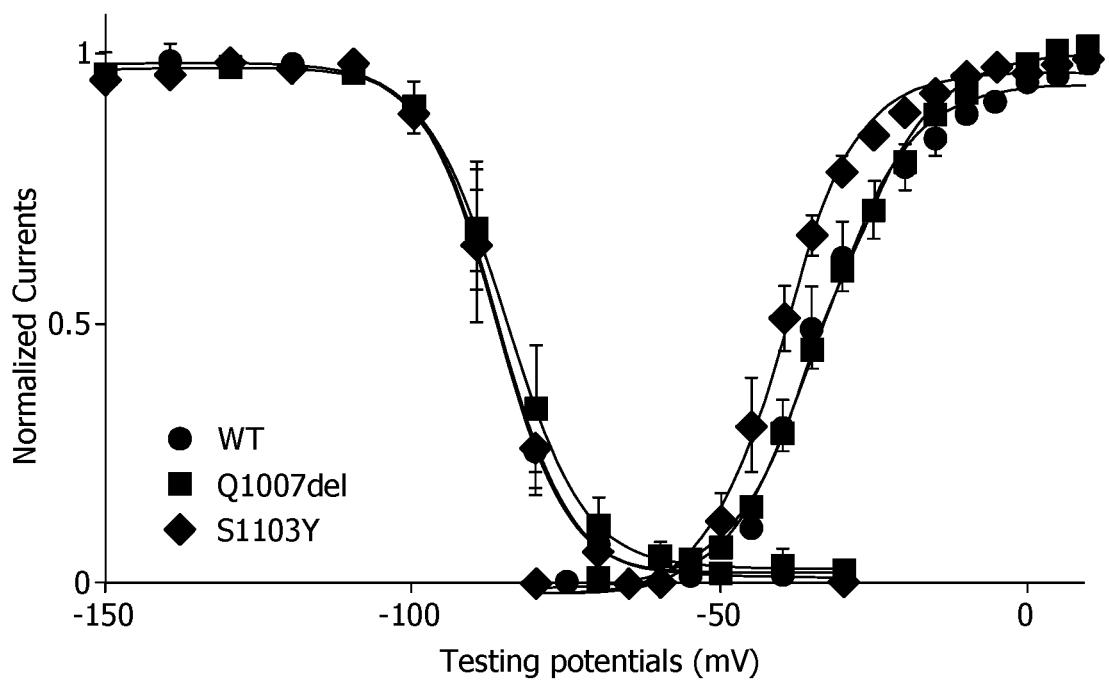

FIG. 17A is a graph illustrating that WT and Q1077del channels have comparable GV curves, while the S1103Y slightly shifts the GV curve to the hyperpolarizing potentials.

Figure 17B:
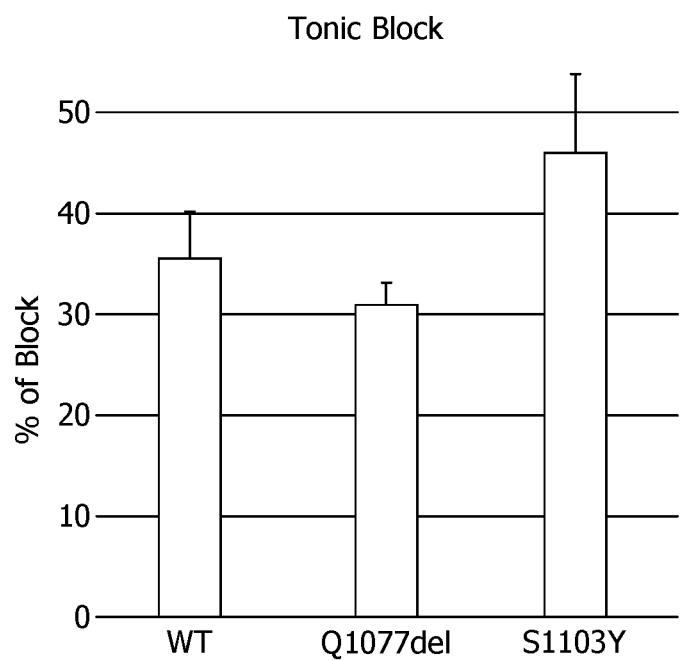

FIG. 17B is a graph illustrating that neither the Q1077del or the S1103Y variant affect steady-state activation, the WT and Q1077del channels exhibit similar tonic block (TB) by 50 uM lidocaine, and the S1103Y variant shows 30% increase in TB compared to WT channels.

Figure 17C:
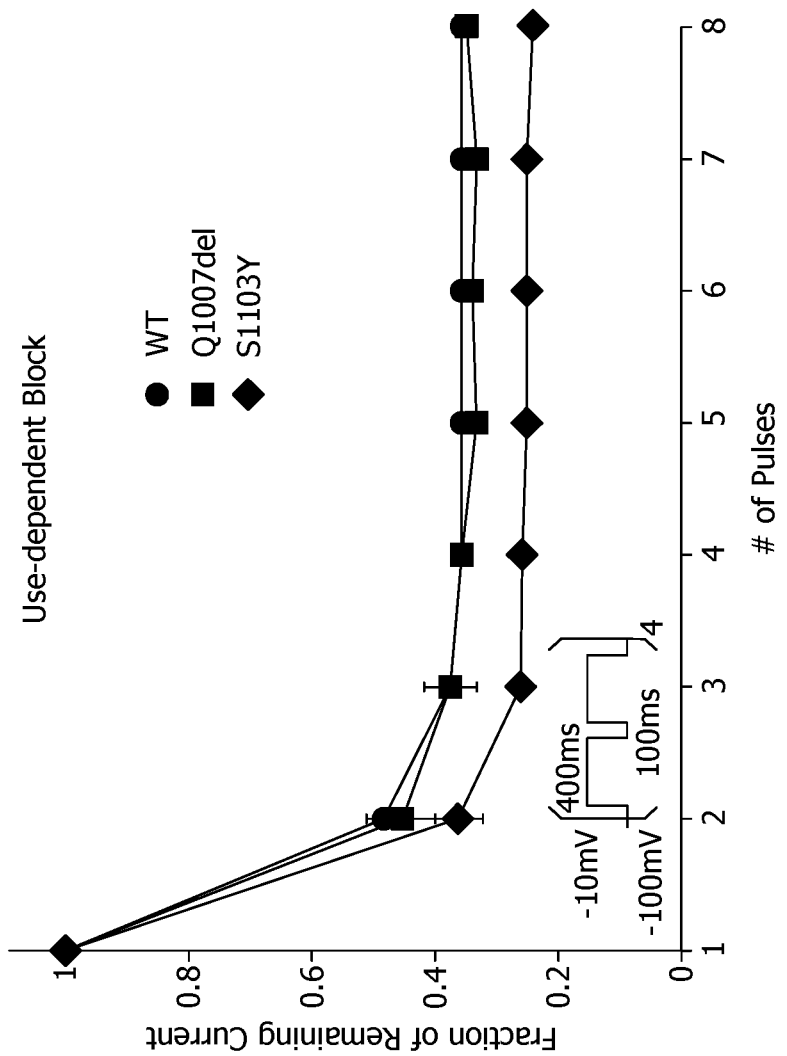

FIG. 17C is a graph illustrating that neither the Q1077del or the S1103 variant affect steady-state activation, the WT and Q1077del channels exhibit similar use-dependent block (UDB) by 50 uM lidocaine, and the S1103Y variant shows 17% increase in UDB, compared to WT channels.

Figure 18A:
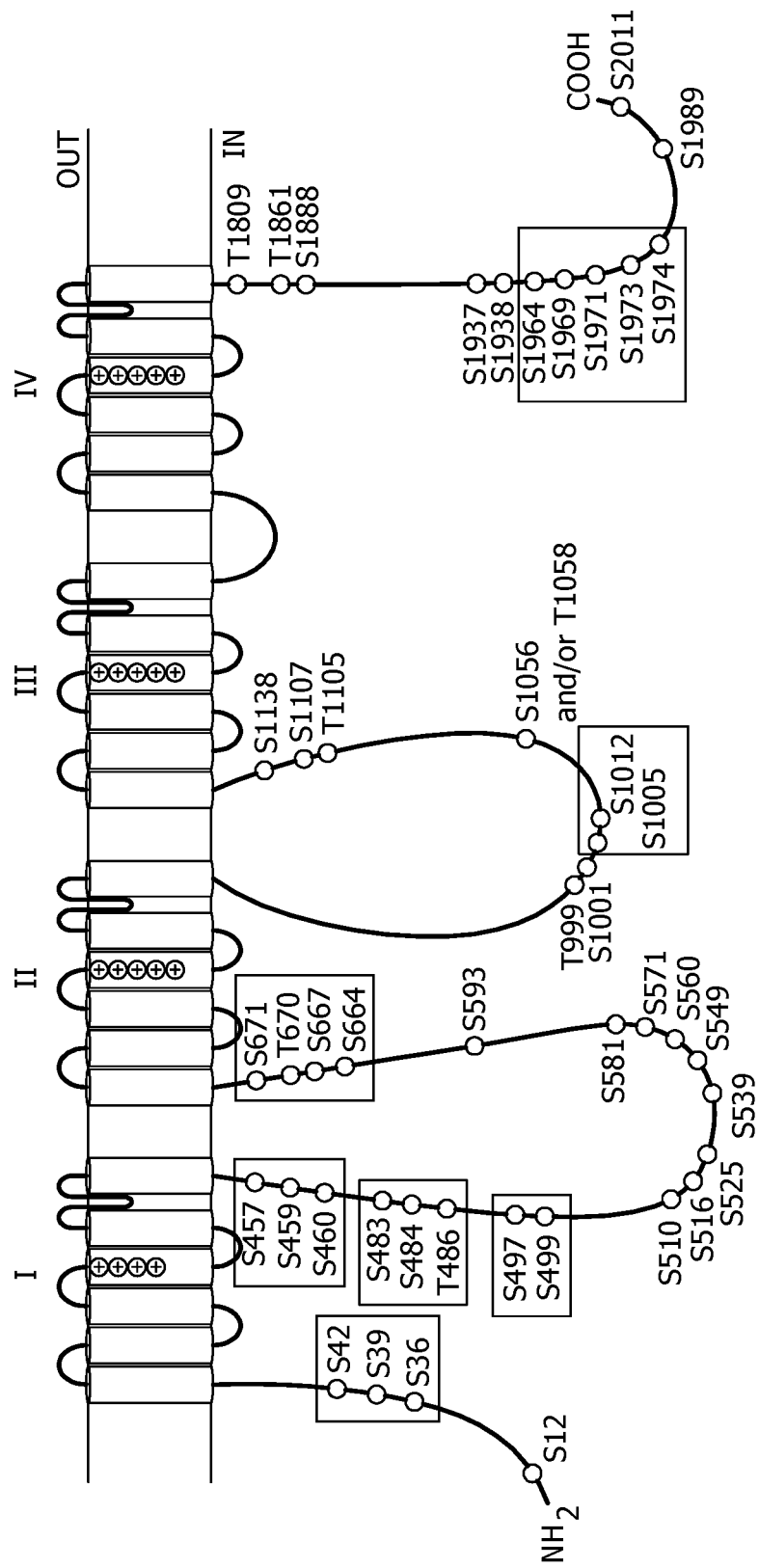

FIG. 18A is a schematic representation of the locations of MS-identified in situ phosphorylation sites on the mouse ventricular Nav1.5 channel protein. Seven clusters of phosphorylation (framed) are detected.

Figure 18B:
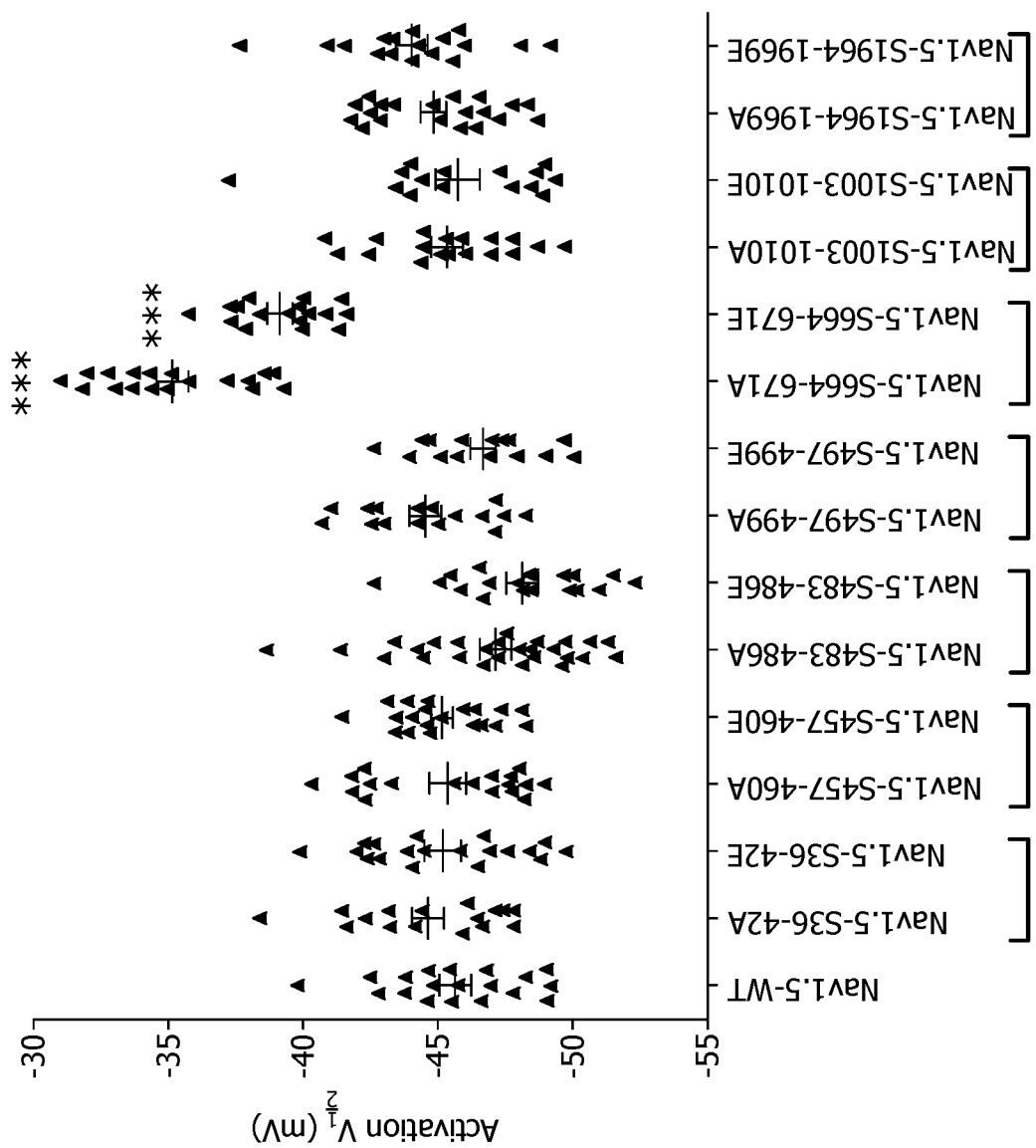

FIG. 18B is a graph illustrating activation V1/2 (in mV) for WT, phosphosilent (Serine to Alanine) and phosphomimetic (Serine to Glutamate) in transiently transfected HEK293 cells. Activation S664-671 phosphosilent channel is depolarized, suggesting that phosphorylation hyperpolarizes activation.

Figure 18C:
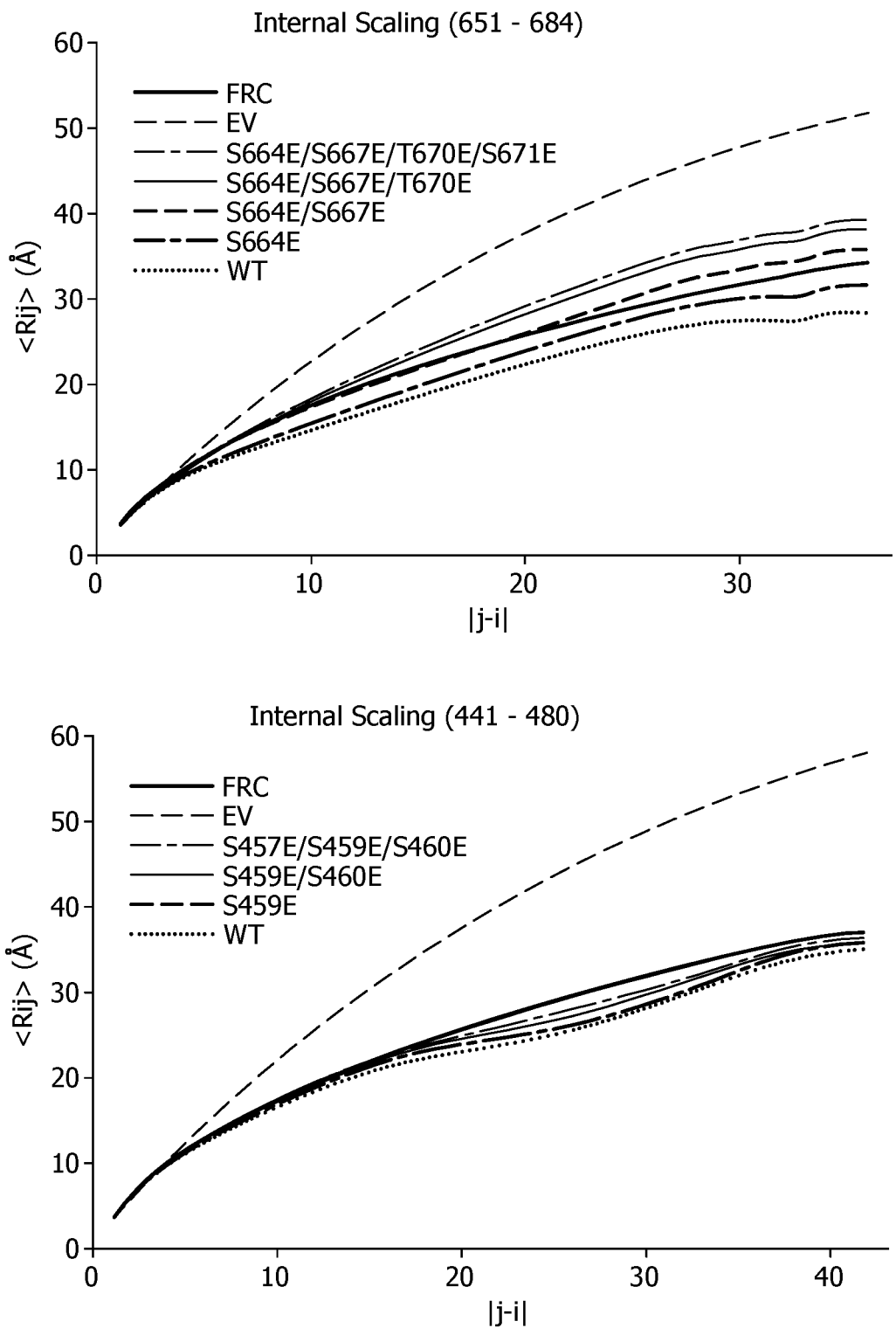

FIG. 18C is a set of graphs illustrating CAMPARI simulations of Nav1.5 residues showing average spatial distances between residues separated by |j−i| sequential positions. The excluded volume (EV) and Flory random coil (FRC) curves are used as reference points. In an EV simulation, all non-repulsive, non-bonded interactions are ignored, providing an approximation of the "upper limit" of expansion for the given protein sequence. In a FRC simulation, all non-bonded interactions are ignored, resulting in an approximate dividing line between more compact and more expanded conformational preferences. Residues 441-480 show relative insensitivity to introduction of phosphomimetic residues, consistent with experiment. In contrast S66-S671 phosphomimetic causes a substantial change.

FIG. 19A is a graph illustrating iPSC-derived cardiomyocytes display sinoatrial (SA) node-, atrial-, or ventricular-like properties (left). Na+ currents were recorded from a myocyte that had been cultured for several weeks (right).

FIG. 19B is an image of iPSC-CMs on the surface of microelectrode array (60MEA200) and a graph of a representative recording of field potential of iPSC-CMs. The cells were treated with hERG blocker E4031. In the graph, the field potential duration was prolonged (arrow) after E4031.

Figure 19C:
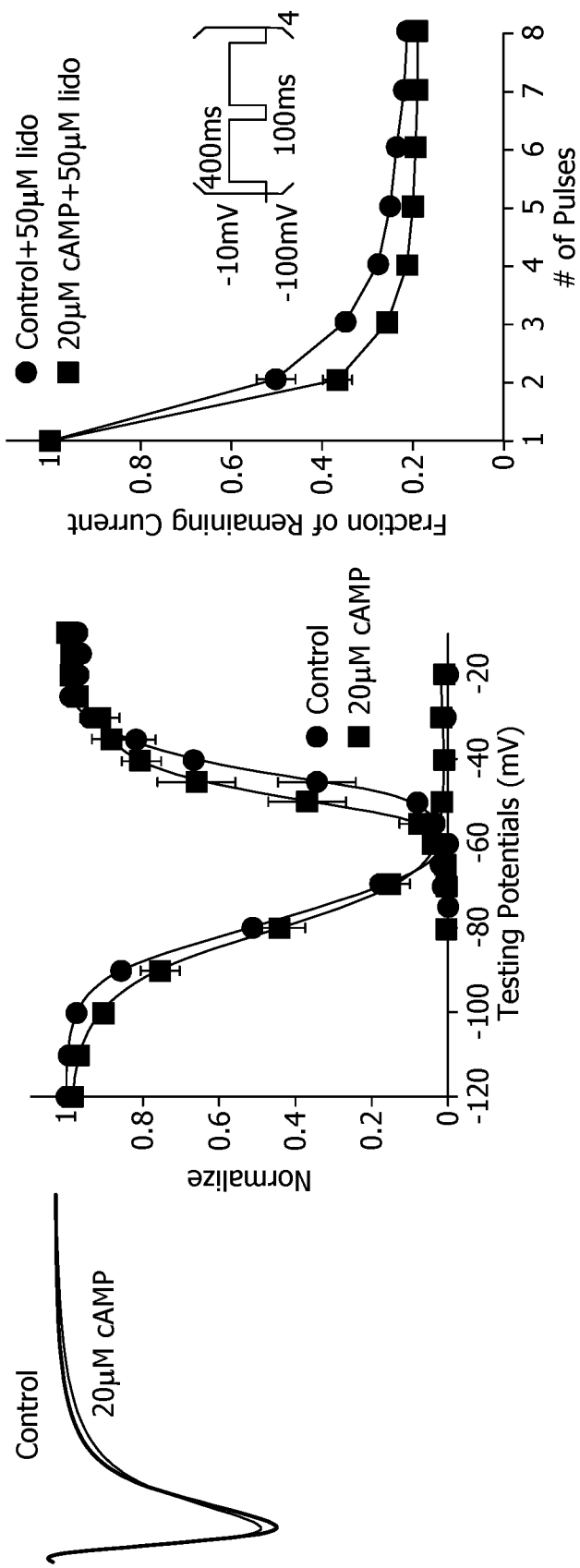

FIG. 19C is a set of graphs illustrating Na+ current from iPSC-CMs in the presence of cAMP shows altered kinetics (left) and a leftward shift in activation, consistent with previous reports. Application of 50 uM lidocaine shows altered use-dependent block kinetics with cAMP.

DETAILED DESCRIPTION OF THE INVENTION

Sodium ion channel blockers are a class of drugs that inhibit the influx of sodium through a cell membrane. This slows the rate and amplitude of the initial rapid depolarization, reduces cell excitability and reduces conduction velocity. They are often used to treat cardiac arrhythmias, supraventricular tachycardia, ventricular tachycardia, or ventricular fibrillation. They are also used as antiepileptic agents and as local anesthetics.

Mexiletine, an oral Class Ib agent, is commonly prescribed to patients suffering from ventricular tachycardia (VT) and with a predisposition to sudden cardiac death, but who have a suboptimal response to β-blockers and the multi-targeted antiarrhythmic amiodarone. Studies have shown that the efficacy of mexiletine and other sodium ion channel blockers is patient specific. However, the reason behind the patient specificity is poorly understood, resulting in an inability to predict drug outcomes for a given patient. A better understanding of class Ib drug action is needed to develop precision medicine for management of ventricular tachycardia. A well-defined example of mexiletine's variable efficacy is the LQT3 syndrome, an inherited arrhythmia syndrome caused by mutations in the SCN5A gene. Unlike other LQT syndromes, LQT3 patients usually experience episodes of ventricular tachycardia during rest and bradycardia. Mexiletine is an effective therapy in suppressing arrhythmia events in some of these patients. However, patients carrying different SCN5A variants show varying QT interval shortening with mexiletine therapy, suggesting that the genetic variants perturb the channel in diverse ways to alter the mexiletine-channel interaction and thus drug efficacy.

The molecular mechanism of drug action was investigated by determining how $Na_V1.5$ mutations alter the sensitivity to mexiletine. Showed herein is that the DIII-VSD conformation plays a role in determining mexiletine blockade. A model is proposed where an activated DIII-VSD causes the channel pore to remain in a partially open conformation that promotes mexiletine TB. Among the 15 common LQT3 variants tested, many variants altered the DIII-VSD conformation, despite their distal locations to the DIII-VSD. It was observed that mexiletine TB strongly correlated with the voltage dependence of DIII-VSD activation but not with SSI, which further suggests that the DIII-VSD conformation rather than closed state inactivation of the channel controls the sensitivity to mexiletine TB.

To predict patient-specific response to sodium ion channel blockers, and, in some aspects, specifically to mexiletine, a PLS regression model was developed. With data collected from 15 LQT3 variants and WT channels, a model was developed that accurately predicted mexiletine UDB and patients' QTc shortening from measured channel gating parameters. Surprisingly two gating processes, DIII-VSD activation and slow recovery from inactivation, influenced both predictions, suggesting that they play a role in modulating the dynamic interactions of sodium ion channel blockers and, in some aspects, mexiletine, with the ion channel.

The modulated receptor theory proposed by Hille has been applied for 40 years to describe class Ib drug interaction with $Na_V$ channels. This theory includes three basic and modulated channel states that illustrate drug interactions with the channel pore: closed, open, and inactivated. The modulated receptor theory emphasizes the primary role of the inactivation gate in promoting and stabilizing drug blockade. As more information regarding channel structure has become available, it is apparent that many conformational changes that are spread throughout the channel work together to cause channel gating. The four VSDs exhibit varied behavior during gating, and each is coupled to the channel pore. Thus, subtle changes in VSD dynamics can affect pore conformation and vice versa.

Definition of Gating Parameters

The following definitions of the gating parameters are used herein. These gating parameters can be measured using various electrophysiology techniques including, but not limited to, patch clamp, cut-open, and two electrode voltage clamp methods. For additional information on these and related material see *JOVE*, 85, e51040 (March 2014) titled "The *Xenopus* Oocyte Cut-Open Vaseline Gap Voltage-clamp Technique With Fluorometry" which is incorporated by reference herein in its entirety for all purposes.

DIII-VSD activated at resting and DIII-VSD V1/2: the DIII-VSD responds to changes in membrane potential and can be in deactivated or activated conformations. As the membrane potential increases the fraction of activated VSDs increases. Cardiac myocytes have a resting potential near −100 mV. DIII-VSD activated at resting measures the fraction of DIII-VSDs in the activated conformation at this resting potential. DIII-VSD V1/2 parameter describes the voltage at which half of the DIII-VSD are at the activated conformation. Both parameters are quantified from the DIII-VSD fluorescence-voltage (F-V) curves that plot the normalized activation of the VSD against voltage.

DIII deactivation τ: upon membrane repolarization, the DIII-VSDs transit from the activated to deactivated conformations. The transition is reflected as the exponential decay in the fluorescence signal. DIII deactivation τ is the time constant of this fluorescence decay, when it is fitted with single exponential equation:

$$y = C - A * \exp\left(-\frac{t}{\tau}\right).$$

SSI V1/2 and inactivation at resting: Na$^+$ channels enter a non-conducting state called inactivation upon depolarizing potentials. As the membrane potential increases, more channels enter this state, which is measured by the steady-state inactivation protocol (SSI). The inactivation at resting parameter measures the fraction of channel that are still conducting when membrane potential is at −100 mV. SSI V1/2 describes at the voltage where half of the channels are in the inactivated state.

Inactivation τ: the inactivation τ measures the kinetics of the fast inactivation process. It is quantified by fitting the current traces with single exponential equation:

$$y = C - A * \exp\left(-\frac{t}{\tau}\right).$$

Slow recovery τ, fast recovery τ, and slow recovery contribution: Na+ channels recover from non-conducting inactivated state at negative potentials. The recovery kinetics at negative potentials are well-fit by two exponential components:

$$y = C - Af * \exp\left(-\frac{t}{\tau f}\right) - As * \exp\left(-\frac{t}{\tau s}\right).$$

The slow recovery τ is the magnitude of the time constant of the slower recovery component. The fast recovery τ is the time constant of the fast component.

Late INa and late INa at 150 ms: despite Na+ channel inactivation process eliminates majority of the current, there is still some residual current. The amount of residual current after fast inactivation is known as late INa. Late INa can be altered by different disease mutations. Late INa parameter measures the residual current left at 50 ms post depolarizing voltage pulse. It is normalized against the peak INa. Late INa at 150 ms measures the residual current at 150 ms post depolarizing voltage pulse.

DIV-VSD V1/2: similar to the DIII-VSD, the DIV-VSD also respond to membrane potential and changes between the deactivated and activated conformations. The DIV-VSD V1/2 measures the membrane voltage at which half of the DIV-VSDs are in the activated conformation.

DIV-VSD activation τ: this parameter describes the kinetics of the DIV-VSD activation. It is quantified by fitting the DIV-VSD fluorescence signal in response to membrane depolarization with single exponential equation:

$$y = C - A * \exp\left(-\frac{t}{\tau}\right).$$

Previous studies showed that lidocaine binding to the pore affected DIII-VSD dynamics. It is demonstrated that LQT3 variants alter the voltage dependence of the DIII-VSD activation, and channels that populated an activated DIII-VSD conformation exhibit increased mexiletine block. To form a more complete understanding of channel and class Ib drug interactions, various components of the channel were considered. Based on these results, an updated modulated receptor model was developed that describes how conformations of the DIII-VSD, the pore, and the inactivation gate alter class Ib drug blockade. In this updated model, 5 states are included: CR (pore closed, DIII-VSD resting), CA (pore closed, DIII-VSD activated), OA (pore open, DIII-VSD activated), IA (pore inactivated, DIII-VSD activated), and IR (pore inactivated, DIII-VSD resting (FIG. 7). Drugs can block the channel from each state, but with different binding and unbinding affinities. When channels are in the CR state, drugs have a low binding rate, because the hydrophilic pathway is unavailable. When the DIII-VSD activates, channels enter the CA state, in which drugs have much higher accessibility to the pore. Finally, in the channel open (OA) and inactivated (IA) states drugs exhibit very high binding rates. After membrane repolarization, channel recovery from inactivation has slower kinetics compare to the DIII-VSD deactivation, causing the channel to enter the IR state. Drugs have both low binding and unbinding rates when the channel occupies this state. When channels are in CR and IR states, only the hydrophobic pathway is accessible.

Due to the structural similarity between lidocaine and mexiletine, patients with ventricular tachycardia that respond well to intravenous lidocaine are often prescribed mexiletine for long-term treatment. However, mexiletine fails to prevent arrhythmia in a large fraction (50%) of these patients, and even induces severe arrhythmia in some cases. This clinical outcome suggests that mexiletine and lidocaine have distinct interactions with the channel that were not previously defined. Notably, mexiletine (pK$_a$ 9.52) is mostly hydrophilic, whereas lidocaine (pK$_a$ 7.6) is partly hydrophobic at physiological pH. These results show that the activated conformation of the DIII-VSD is required for a hydrophilic drug, but not for a hydrophobic drug, to access the channel pore. Many LQT3 variants stabilize the DIII-VSD in its activated position, promoting mexiletine block through the hydrophilic voltage-dependent pathway, which explains why mexiletine is effective in managing LQT3 syndrome. In contrast, for treating ventricular tachycardia patients with normal Na$_V$1.5 channels that do not have activated DIII-VSDs, mexiletine may be less effective than lidocaine. These results suggest that response to lidocaine may not be a good predictor of the clinical response to mexiletine therapy.

Demonstrated herein are several LQT3 variants that are insensitive to mexiletine due to the less activated DIII-VSD conformation of the channel. To rescue their insensitivity, a new therapeutic strategy that uses a combination of drugs can potentially be employed. A drug that promotes DIII-VSD activation can be used in combination with mexiletine to improve antiarrhythmic efficacy in the insensitive variants. Several combination therapies of Na$^+$ channel blockers have been tested in clinical settings. For instance, an early study suggested that a combination of oral mexiletine and flecainide prevents recurrence of ventricular tachycardia in patients that are nonresponsive to monotherapy. Without being bound by a specific theory, it is thought that flecainide improves mexiletine efficacy by promoting DIII-VSD activation. However, the mechanism of why certain combinations improve efficacy is not known.

For more general ventricular arrhythmias other than LQT3 syndrome, mexiletine is commonly prescribed to patients with recurrent ventricular tachycardia post myocardial infarction and ischemic heart diseases that are resistant to other conventional antiarrhythmic agents. Although mexiletine effectively suppresses episodes of premature ventricular contraction (PVC), it induces adverse side effects in some patients resulting in them withdrawing from therapy. Side effects include severe nausea and tremor. The incidence of side effects is dosage dependent. It is possible that higher doses are needed to suppress ventricular tachycardia in these patients, because they have wild-type $Na_V1.5$ channels, which are not as sensitive as some LQT variants. The patient-specific responses can be attributed to disparity in expression of $Na_V1.5$ isoforms (polymorphisms) and accessory $Na_V\beta$ subunits. To reduce the side effects of mexiletine, the dose must be lowered while preserving its blocking efficiency.

Data-driven modeling is commonly applied in the field of systems biology due to the large-scale nature of non-intuitive experimental data from biological assays, such as microarray and gene sequencing. Because ion channels are complex systems where many parts of the channel work in concert to generate time and voltage dependent gating, a data-drive model would be very useful in analyzing the many complex interactions therein. Different voltage protocols can isolate different channel gating processes. Although effective, these voltage protocols are not ideal, because the properties they measure overlap. For example, an inactivation change can affect protocols that measure activation by shutting down channels before the channels open maximally. Statistical tools that can reduce data dimensionality, such as principal component analysis and partial least square regression can reduce redundant information in data recorded with different voltage protocols.

In addition to dimensionality reduction, the methods applied herein have the advantage of recognizing the multivariate relationships between input (independent) and output (dependent) variables. It rotates the input data to new optimal dimensions that maximize the covariance between input and output data. Thus, PLS regression models can be trained with existing data, and then used to predict output of new input data. Disclosed herein is a PLS regression model that predicts sodium ion channel blocker response using channel gating parameters. In some aspects, the PLS regression model predicts the mexiletine response using channel gating parameters.

In one aspect, disclosed herein is a method for predicting a patient response to a sodium ion channel blocker when the patient has LQT syndrome and/or arrhythmia including ventricular arrhythmia. The method generally comprises: determining a plurality of parameters associated with sodium ion channels; generating a model for patient response by using a partial least squared (PLS) regression analysis on said plurality of parameters; and using the model to predict the patient response if the patient is administered the sodium ion channel blocker.

In some aspects, the sodium ion channel blocker is selected from the group consisting of ranolazine, phenytoin, disopyramide, lidocaine, mexiletine, triamterene, lamotrigine, amiloride, moricizine, oxcarbazepine, quinidine, procainamide, tocainide, amiodarone, propafenone, eclazine, flecainide, encainide, ajmaline, aprindine, tetrodotoxin, eslicarbazepine acetate, pilsicainide, and eslicarbazepine. In some aspects, the sodium ion channel blocker is lidocaine. In some aspects, the sodium ion channel blocker is mexiletine.

In some aspects, the sodium ion channel blocker is a compound that fits into the pharmacophore developed for local anesthetics as described in Becker, et al., Anesth. Prog., 53, 98 (2006) which is incorporated by reference herein. The pharmacophore comprises three aspects—a lipophilic aromatic ring, a linking ester or amide, and a terminal amine. Without being bound by a specific theory, it is thought that the aromatic ring improves the lipid solubility of the compound while the terminal amine renders the compound water soluble either through salt formation or quaternization. The ester or amide contributes to the length of action for the compound based on its metabolic stability.

In some aspects, the methods of the present disclosure are useful for predicting a patient response to any sodium ion channel blocker. In some forms, the methods comprise generating a model for patient response by using a partial least squared (PLS) regression analysis on a plurality of parameters associated with sodium ion channels. In general, the method comprises the steps of collecting a biological sample from the patient, expressing at least one gene from the biological sample, testing the expressed gene for a plurality of parameters, and using the plurality of parameters in a model to predict the patient response to the sodium ion channel blocker. In some forms, the methods are in vitro methods. In some forms, the patient has LQT syndrome or an arrhythmia. In some forms, the method further comprises determining the plurality of parameters associated with sodium ion channels. In some forms, the at least one gene expresses Nav 1.5. In some forms, the model for predicting a patient response to a sodium ion channel blocker is used when the patient has LQT syndrome or an arrhythmia. In some forms, the plurality of parameters are ion channel gating parameters selected from the group consisting of activation rate, deactivation rate, voltage dependence of activation, voltage dependence of inactivation, inactivation rate, inactivation recovery rate, VSD activation rate, VSD deactivation rate, VSD voltage-dependence, and any combination thereof. In some forms, the sodium ion channel gating parameters may be selected from the group consisting of fraction of DIII-VSD activated at resting, DIII-VSD V1/2, DIII deactivation τ, Steady-state Inactivation, inactivation at resting, inactivation τ, fast recovery τ, slow recovery τ, slow recovery contribution, late INa, late INa at 150 ms, DIV-VSD V1/2, DIV-VSD activation τ, and any combination thereof. This list is not exhaustive and other known gating parameters may be included in the development of the model developed herein.

The different gating parameters may be used alone or in combination with other gating parameters. For example, the PLS regression model may be done using 2 parameters, using 3 parameters, using 4 parameters, using 5 parameters, using 6 parameters, using 7 parameters, using 8 parameters, using 9 parameters, using 10 parameters, using 11 parameters, using 12 parameters, using 13 parameters, or even all 14 parameters. In some aspects, the PLS regression model uses from 2 to 14 parameters in a first iteration of the model and then reduces the overall total number of parameters. As part of the initial model development, the PLS model may use all 14 parameters and full analysis of the data reveals that less than 14 of the parameters are required to provide a good predictive model. For example, in some aspects the final PLS model only uses two parameters, such as, for example, DIII-VSD $V_{1/2}$ and slow recovery τ in order to predict patient response to a sodium ion channel blocker. In some aspects, the PLS model only uses two parameter in order to predict patient response to mexiletine.

As with any PLS regression model, the value of the cross-validate $Q^2$ determines the usefulness and validity of the model. In some aspects disclosed herein, the cross-validate $Q^2$ of the PLS model for predicting patient response to the sodium ion channel blocker is greater than 0.3, greater than 0.4, greater than 0.5, greater than 0.6, greater than 0.7, greater than 0.8, or even greater than 0.9. The number of parameters uses in constructing the model and the relevance of those parameters affects the value of the cross-validate $Q^2$. As such, other gating parameter as are known in the art may be used to develop and further improve the model disclosed herein.

Because the model is being developed to predict the patient response to sodium ion channel blockers, the output of the model should be relevant to a parameter in patient care. In some aspects, the patient response is calculated as a $\Delta QT$ as measured by an electrocardiogram. Other parameters relevant to the heart condition of a patient as are known in the art may also be used.

In another aspect, disclosed herein is an in vitro method for predicting a patient response to a sodium ion channel blocker when the patient has LQT syndrome and/or arrhythmia including ventricular arrhythmia. The method generally comprises: collecting a biological sample from the patient; expressing at least one gene from the biological sample; testing the expressed gene for a plurality of parameters; and using the plurality of parameters in the model to predict the patient response to the sodium ion channel blocker. In some aspects, the model is the PLS regression model as described elsewhere herein.

In some aspects, the sodium ion channel blocker is selected from the group consisting of ranolazine, phenytoin, disopyramide, lidocaine, mexiletine, triamterene, lamotrigine, amiloride, moricizine, oxcarbazepine, quinidine, procainamide, tocainide, amiodarone, propafenone, eleclazine, flecainide, encainide, ajmaline, aprindine, tetrodotoxin, eslicarbazepine acetate, pilsicainide, and eslicarbazepine. In some aspects, the sodium ion channel blocker is lidocaine. In some aspects, the sodium ion channel blocker is mexiletine.

In some aspects of the in vitro method, the at least one gene is a gene selected from the group consisting of sodium ion channels, caveolin-3, alpha 1 syntrophin, glycerol-3-phosphate dehydrogenase, a beta subunit 1 of a sodium ion channel, a beta subunit 2 of a sodium ion channel, a beta subunit 3 of a sodium ion channel, a beta subunit 4 of a sodium ion channel, ankyrin-G, Syntrophin proteins, MOG1, Nedd4-like calmodulin kinase II, protein tyrosine phosphatase H1, FHF1B, Calmodulin, GPD1L, Telethonin, and plakophilin-2. In some aspects of the in vitro method, the at least one gene is a gene that expresses a sodium ion channel. In some aspects, the gene expresses the $Na_V 1.1$ ion channel. In some aspects, the gene expresses the $Na_V 1.2$ ion channel. In some aspects, the gene expresses the $Na_V 1.5$ ion channel. In some aspects, the gene expresses the $Na_V 1.6$ ion channel. In some aspects, the gene expresses the $Na_V 1.8$ ion channel.

With these novel findings of how channel gating dynamics affects the sodium ion channel blockade, a PLS regression model was built that uses channel gating parameters to more specifically predict patient-specific response to mexiletine. It incorporates this regression model into a mexiletine $QT_c$ calculator that can output the patient's predicted $QT_c$ after mexiletine therapy. The calculator gives users a warning if the patient is predicted to still have high-risk $QT_{c2}$ (>500 ms) after therapy. In a blind clinical trial, the calculator accurately predicted the majority of patients' post-mexiletine $QT_c$, except for a patient with very long baseline $QT_c$. Even though mexiletine reduces $QT_c$ in these patients, they still have high-risk $QT_c$ post therapy, suggesting it is necessary to apply mexiletine in conjunction with additional therapies, such as implantable cardioverter-defibrillator. Overall, this understanding of the mexiletine molecular mechanism can be applied to predict patient-specific response to mexiletine, which can improve clinical outcomes of LQT3 management through a precision medicine approach.

Examples for LQT3

Molecular Biology cRNA for human $Na_V 1.5$ $\alpha$ subunit was produced from the pMAX vector. All mutagenesis was achieved using overlap extension PCR reaction, followed by In-fusion cloning (Clonetech). All mutations were confirmed with sequencing (Genewiz). Each plasmid was then linearized with PacI restriction enzyme. Capped mRNA was synthesized using the mMESSAGE mMACHINE T7 Transcription Kit (Life Technologies) and purified via phenol-chloroform extraction.

Voltage Clamp Fluorometry

Four previously developed constructs for VCF were used in recordings (DI: V215C, DII: S805C, DIII: M1296C, and DIV: S1618C). mRNA of the $Na_V 1.5$ channel constructs were co-injected with the $Na_V$ $\beta 1$ subunit in *Xenopus* oocytes. Voltage clamp recordings were performed 4-5 days after injection. The recording set-up, solutions, and recording protocols for VCF are as described previously. Mexiletine hydrochloride powder (Sigma) was dissolved in extracellular recording solution to a stock concentration of 4 mM. pH for the solution is adjusted to 7.4. Mexiletine was further diluted from the stock solution to various concentrations (2-1000 μM). During recordings, measurements were made from the same cell before and after addition of the indicated concentration of mexiletine. Mexiletine was manually perfused into the extracellular solution chamber in the cut-open voltage clamp set-up.

Electrophysiology Data Analysis

Data analyses were performed with Clampfit (v10; Molecular Devices), MATLAB (R2012a; MATLAB), and Excel (Microsoft). G-V, fluorescence-voltage (F-V), and SSI curves were quantified by fitting a Boltzmann function:

$$y=1/(1+\exp((V-V_{1/2})/k)).$$

DIII-VSD deactivation rate was quantified based on the time to 50% decay. Channel recovery from inactivation was fitted with a sum of exponents function:

$$y = C - Af * \exp\left(-\frac{t}{\tau f}\right) - As * \exp\left(-\frac{t}{\tau s}\right),$$

which accounts for both fast and slower components of recovery. Comparison between conditions or constructs were performed using paired or independent student t test, respectively (Microsoft Excel). The error bars shown in the figures represent the standard errors of mean (SEM).

Partial Least-Squares Regression

Channel parameters (predictor variables) and channel responses to mexiletine (response variables) were standardized using z-score transformation. Partial least-square (PLS) regression was performed using MATLAB function "plsregress". Model stability was examined with leave-one-out cross validation. Each perturbation (channel variant) is individually removed from the dataset, and a PLS regression model is built on the rest of the variants. Using this model, mexiletine responses are predicted for the removed variant and compared with the measured responses. The model's general ability to predict left-out data was measured by calculating the Q-squared ($Q^2$) values, which is the sum of squares of the difference between predicted and real values, normalized by the total variability in data. Variable importance in the projection (VIP) scores for each gating parameter is ranked by its impact on model fitness ($Q^2$). One gating parameter is removed at a time, and cross-validated model fitness $Q^2$ is calculated for the model based on the rest of parameters. The lower the is, the higher VIP score the gating parameter has.

Mexiletine $QT_c$ Shortening Calculator

The final model containing all training dataset with reduced features for predicting $QT_c$ shortening (DIII-VSD activation and slow recovery τ) was implemented in a user-interface. When the gating parameters for a new variant are entered into the calculator, they are normalized with the training dataset. The predicted percentage of $QT_c$ shortening is multiplied with patient's baseline $QT_c$ for calculating predicted post-mexiletine $QT_c$.

Blind Retrospective Clinical Trial

All the predictions were made without prior knowledge of clinical outcomes. Predictions were made based on patient $QT_c$ baseline and their genetic variants. After measuring mutant channel gating properties, parameters were entered into the mexiletine $QT_c$ shortening calculator, which then predicted post-mexiletine $QT_c$ intervals. The predicted values were then compared to clinical data.

Results

Mexiletine Stabilizes the Active Conformation of the DIII-VSD

The response to mexiletine was similar for some properties and different for others of the class Ib antiarrhythmics. Like other class Ib antiarrhythmics, mexiletine preferentially inhibited the late component of the Na$^+$ current ($I_{Na}$) compared with the effect on the peak current (FIG. 1A, top). Mexiletine also exhibited UDB (FIG. 1A, bottom), which is a property of class Ib antiarrhythmics that is reflected by an increase in the inhibitory effect as the channels are repetitively activated by depolarizing voltage pulses.

Binding of class Ib drug lidocaine to the channel results in stabilization of the inactivated state, which is often reflected by a hyperpolarizing shift in the steady state inactivation (SSI) curve. In contrast to lidocaine, mexiletine caused a minimal shift of the SSI curve (FIG. 1B). However, similar to lidocaine, mexiletine delayed recovery from inactivation, especially the slow component of recovery (FIG. 1C). Thus, mexiletine appeared to influence the inactivated state through a mechanism different from that of lidocaine.

Figure 1D:
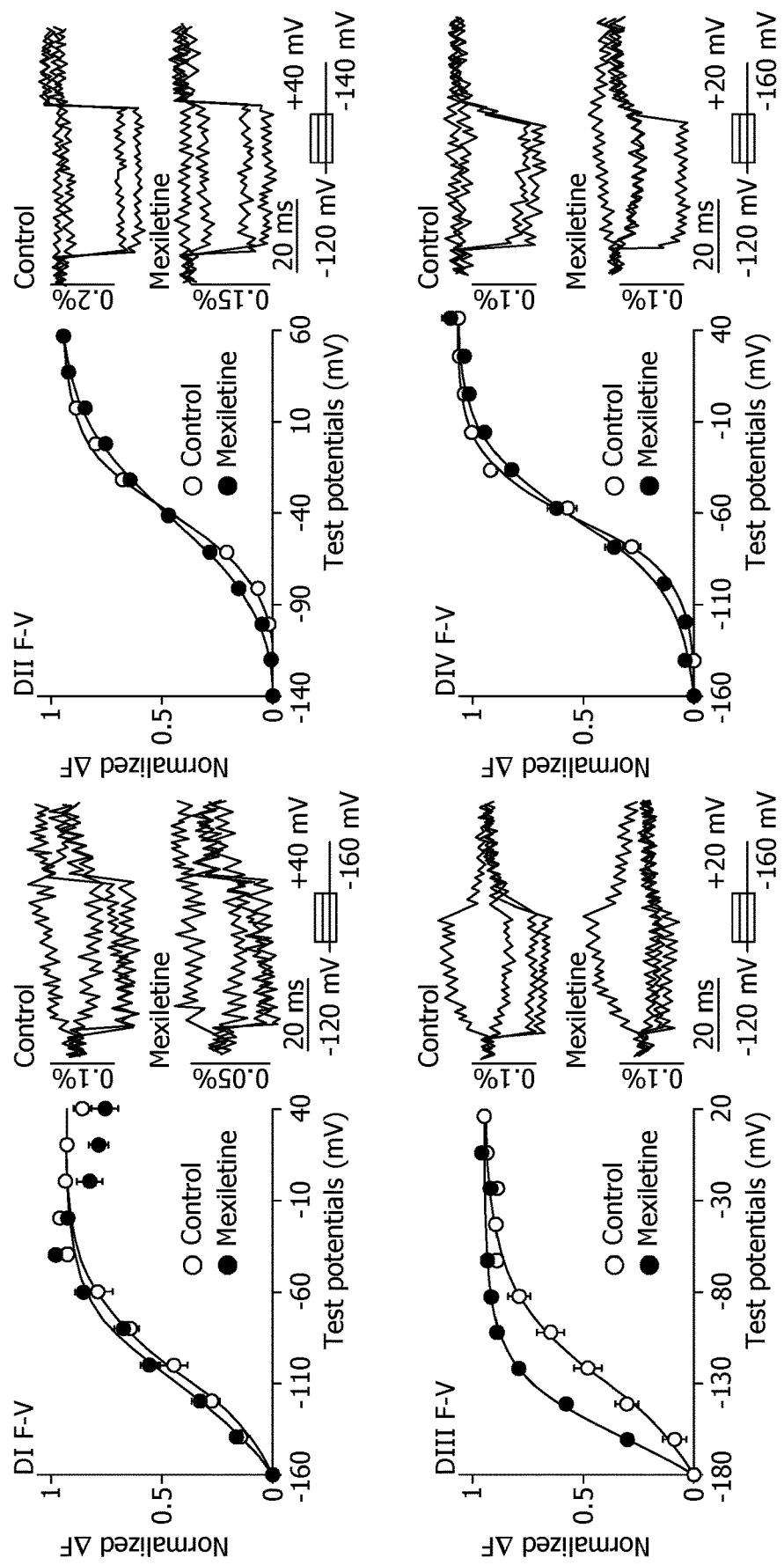
FIG. 1D are a series of graphs illustrating (left panels) the voltage dependence of steady-state fluorescence (F-V curves) from four domains (DI-V215C, DII-S805C, DIII-M1296C, DIV-S1618C) before (control, open circles) and after (mexiletine, closed circles) 4 mM mexiletine. Fluorescence after mexiletine was measured after 80% tonic block. Also shown are (right panels) representative fluorescence traces before and after mexiletine. Mexiletine only affects DIII-VSD by causing a hyperpolarizing shift in DIII F-V curve and slows down DIII-VSD deactivation, without affecting other three domains.

Previously, multiple studies demonstrated that lidocaine block of Na$_V$ channels enhances the stability of the DIII-VSD activated conformation. Here, the interaction of mexiletine was tested with the Na$_V$1.5 VSDs by voltage-clamp fluorometry (VCF). In these experiments, a fluorophore is tethered to the charged S4 segment of one of the four VSDs. As the VSD changes conformation, the environment around the fluorophore is altered, which changes emission from the fluorophore, enabling measurement of the time and voltage dependence of the VSD conformation. The steady-state fluorescence voltage (F-V) curves represent the voltage-dependence of the VSD activated conformation. Among four domains, only the DIII F-V curve displayed a large hyperpolarizing shift ($\Delta V_{1/2}$=−32.5±7.5 mV, p=0.04) after mexiletine block (FIG. 1D), implying that the DIII-VSD remains in an activated conformation at more negative potentials upon mexiletine binding. Comparing the fluorescence traces before and after mexiletine block showed that both DIII and DIV-VSDs have slower activation and deactivation kinetics in the presence of mexiletine (FIG. 1D). Because the DIII and DIV-VSDs are tightly coupled, the mexiletine-induced alteration of the DIV-VSD kinetics may be a consequence of its effects on the DIII-VSD.

Figure 1E:
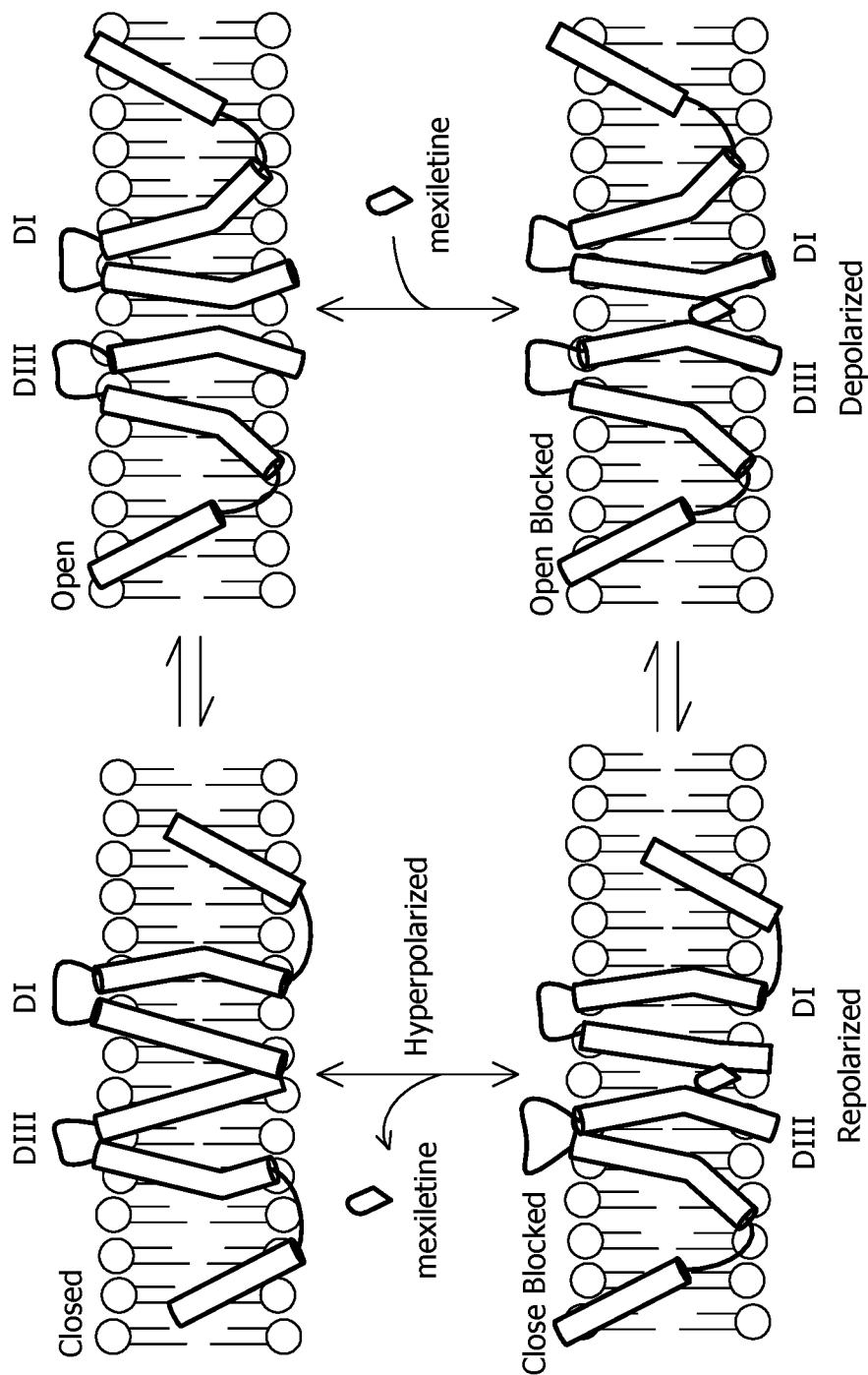
FIG. 1E depicts the proposed schematic (adapted from the Arcisio-Miranda lidocaine model) showing the mechanism of mexiletine stabilization of activated DIII-VSD. Only DI and DIII are shown and the VSDs are represented by a single S4 segment for clarity.

To account for mexiletine's effects on the DIII-VSD, without being bound by any specific theory, a model for its mechanism of action is suggested. Binding of mexiletine within the channel pore prevents the DIII-pore domain (S5-S6) from transitioning to a completely closed conformation during membrane repolarization (FIG. 1E). The partially open conformation of the DIII-pore causes the DIII-VSD to remain in the activated conformation. This is like previously reported mechanisms of the interaction of lidocaine with Na$_V$ channels.

LQT3 Variants with Different Mexiletine Sensitivities have Distinct Voltage Dependence of DIII-VSD Activation To understand the molecular mechanisms underlying differences in mexiletine sensitivity among LQT variants, single point mutations R1626P or M1652R (FIG. 2A) were tested, each of which exhibits a different responses to mexiletine. These two variants exhibited different responses to mexiletine under nonstimulated conditions, tonic block (TB), and under stimulated conditions, use-dependent block (UDB). Consistent with the previous studies, when compared to the effect of mexiletine on WT channels, the drug exerted TB of R1626P at lower concentrations (EC$_{50}$=211.1 μM) and required higher concentrations to exert TB of M1652R (EC$_{50}$=2035.3 μM). Mexiletine had an EC$_{50}$=760.8 μM for TB of WT channels (FIG. 2B).

UDB was assessed by applying 400 ms depolarizing pulses at 2 Hz, mimicking conditions during ventricular tachycardia WT and R1626P have comparable UDB (WT: EC$_{50}$=58.4 μM, R1626P: EC$_{50}$=56.6 μM), while M1652R has much lower UDB (EC$_{50}$=192.7 μM) (FIG. 2C). The UDB of mexiletine was tested using the cut-open voltage clamp. The EC$_{50}$ values observed with this method are higher than those reported using patch clamp analysis of HEK 293 cells. It is thought that this difference is due to limited solution access to the cell membrane in the cut-open voltage clamp set-up during perfusion. To test this hypothesis, the dose responses were measured using two-electrode voltage clamp (TEVC), which allows better access to the solution. TEVC recordings showed mexiletine EC$_{50}$ values for each variant that were similar to previously reported values (Table 1, FIG. 9), suggesting that, in the cut-open set-up, amount of mexiletine at the channel is approximately 3-fold lower than the perfused concentration (Table 1). With this information, the differences in EC$_{50}$ values that relate to methodology can be accounted for.

TABLE 1

Comparing EC$_{50}$ for TB and UBD across different recording set-ups

| | TB EC$_{50}$ (μm) | UBD EC$_{50}$ (μm) |
|---|---|---|
| | cut-open voltage clamp | |
| WT | 760 | 58.4 |
| R1626P | 211 | 56.6 |
| M1652R | 2035 | 192.7 |
| | two-electrode voltage clamp | |
| WT | 449.9 | 36.7 |
| R1626P | 86.3 | 18.5 |
| M1652R | 633.3 | 96.7 |

TABLE 1-continued

Comparing $EC_{50}$ for TB and UBD across different recording set-ups

| | TB $EC_{50}$ (μm) | UBD $EC_{50}$ (μm) |
|---|---|---|
| | patch clamp (HEK 293T) | |
| WT | 253 | 38.0 |
| R1626P | 153 | 8.8 |
| M1652R | 944 | 96.1 |

Figure 2D:
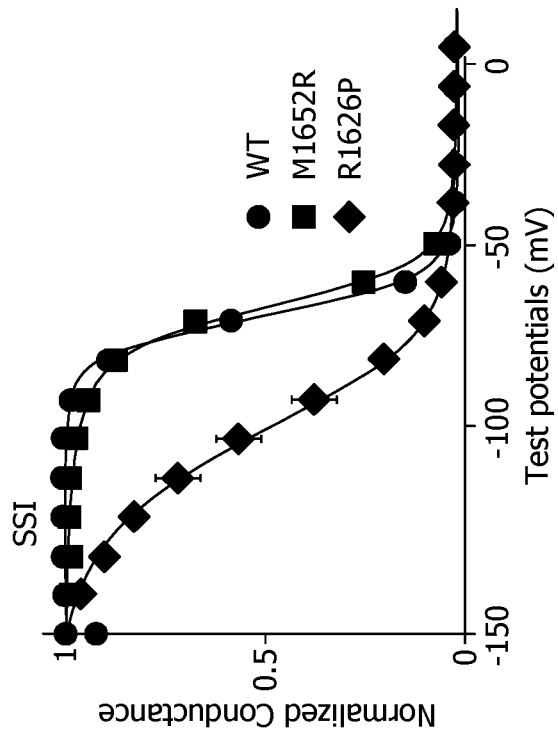
FIG. 2D depicts the voltage dependence of steady-state fluorescence of DIII. DIII F-V curve of M1652R showed depolarizing shift, while R1626P showed hyperpolarizing shift compared to WT channels.

To probe the link between the DIII-VSD conformation and mexiletine block, the correlation between DIII-VSD conformation and sensitivity of the channel to mexiletine was assessed. It was thought that if mexiletine block of the pore caused the DIII-VSD to remain in the activated position, then channels with an activated DIII-VSD conformation would facilitate mexiletine accessibility to the pore. VCF experiments showed that both mutations significantly affected DIII-VSD conformation (FIGS. 2D, 2F), despite their locations in DIV-VSD, which is distant from DIII-VSD (FIG. 2A). Compared to WT channels, the mexiletine-sensitive R1626P mutant exhibited a hyperpolarized DIII F-V curve ($\Delta V_{1/2}$=−38.9 mV, p=0.02), suggesting that more DIII-VSDs were in an activated conformation at the resting membrane potential. Conversely, the mexiletine-insensitive variant M1652R exhibited a depolarizing shift in the DIII F-V curve ($\Delta V_{1/2}$=28.2, p=0.01), indicating that more DIII-VSDs were in deactivated conformation. The shifts in voltage dependence of the DIII-VSD activation mirrored the differences in block by mexiletine. The mutant with DIII-VSD in an activated conformation (R1626P) at the resting potential displayed higher TB. These results support the conclusion of a reciprocal relationship between mexiletine block and DIII-VSD conformation of the mutants.

Figure 2E:
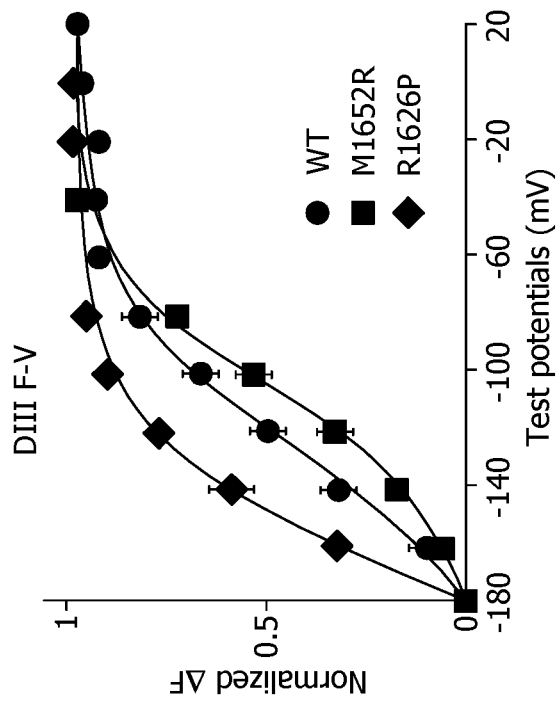
FIG. 2E depicts the steady-state inactivation (SSI) curves of WT, R1626P, and M1652R channels.
Figure 2F:
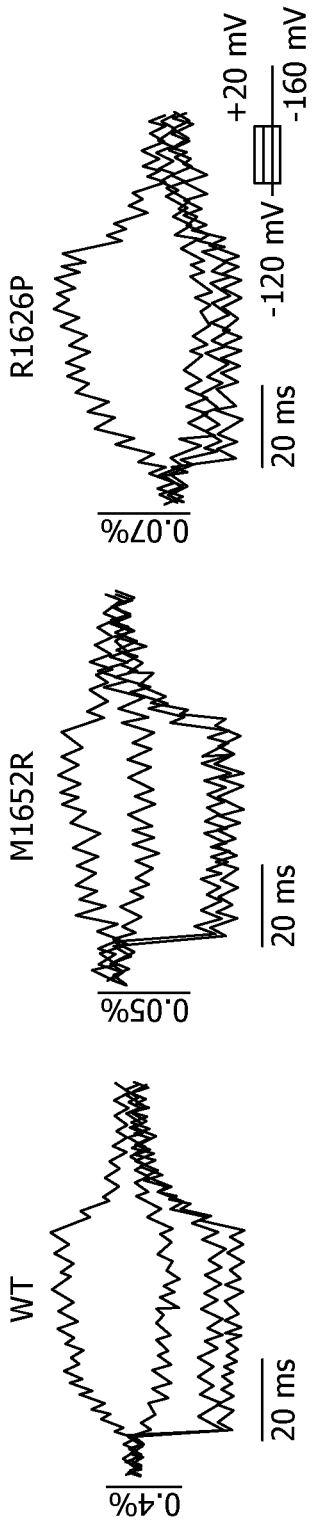
FIG. 2F illustrates representative DIII fluorescence traces from WT-M1296C, M1652R-M1296C, and R1626P-M1296C. All three constructs exhibit distinct fluorescence kinetics and voltage-dependence.

Conventionally, occupancy of the inactivated state has been considered the primary determinant of class Ib drug action. Consequently, the modulated receptor model describes preferential drug binding to channels that are inactivated. To test this idea, different variants that affected the SSI curve were tested. Although the most sensitive mutation R1626P shifted SSI prominently, the magnitude of the shifts by these two variants are not consistent with their differences in mexiletine block (FIG. 2E).

To further test whether the conformation of DIII-VSD regulates mexiletine block independent of inactivation, the TB of WT channels at various potentials ranging from −120 to −90 mV was assessed. At these holding potentials the WT channels exhibited full conductance (none in the inactivated state) (FIG. 2E) and showed a range of DIII-VSD conformations (FIG. 2D). At four different holding potentials, −120, −110, −100, and −90 mV, the channel showed altered TB by mexiletine (FIG. 2H). Moreover, the amount of TB had a linear relationship with the fraction of DIII-VSDs in the activated conformation at those potentials (FIG. 2H). This result shows that the proportion of channels in the inactivated state is not the only factor that determines effectiveness of mexiletine block.

Based on these results, a model was proposed that explains the difference in mexiletine sensitivity between the two LQT variants (FIG. 2G). At resting membrane potential, DIII-VSD of the sensitive variant R1626P tends to occupy the activated conformation. Because the activated conformation of DIII-VSD is coupled to conformation of the DIII-pore, the pore adopts a conformation that facilitates mexiletine accessibility. In contrast, fewer of the DIII-VSDs of the insensitive mutant M1652R are in the activated conformation at these potentials, causing the DIII-pore to remain in a conformation that prevents mexiletine from binding.

Voltage-dependent, not lipophilic, block accounts for differences in mexiletine response among LQT3 variants.

The F1760K mutation eliminates UDB by lidocaine and prevents lidocaine from affecting gating currents. Based on this binding site, Hanck et al. categorized lidocaine block into two components: a voltage-independent lipophilic block and a voltage-dependent block. Lipophilic block is independent of the putative binding site F1760. To determine if difference in the $EC_{50}$ for TB by mexiletine among the R1626P, M1652R, and WT channels is due to lipophilic or voltage-dependent block, their responses to mexiletine in the background of F1760K mutation were tested.

The response of F1760K channels to mexiletine was assessed. Both TB and UDB by mexiletine are greatly reduced for the F1760K channel. Using VCF, it was found that mexiletine did not alter the conformation of DIII-VSD of the F1760K mutant channel (FIG. 8). The mexiletine-induced TB at 500 μM was measured, a concentration at which the difference in TB among the channels was evident (FIG. 2B), in WT, R1626P, and M1652R channels that also had the F1760K mutation. The TB achieved with 500 μM mexiletine in channels with F1760K was similar (FIG. 2I). Thus, the differences in the $EC_{50}$ values for mexiletine among these LQT variants appeared due to voltage-dependent block rather than lipophilic block.

Decoupling the DIII-VSD from the pore eliminates differences in mexiletine blockade among LQT3 variants.

To further understand how the DIII-VSD affects mexiletine block, the A1326W mutation (FIG. 3A) was used, which decouples DIII-VSD from the pore. In channels with A1326W, mexiletine no longer affects the conformation of DIII-VSD (FIG. 10A), demonstrating that a connection between the DIII-VSD and the pore is required to observe the mexiletine effect on DIII-VSD conformation. The hypothesis is that R1626P and M1652R have distinct mexiletine sensitivities due to differences in the voltage dependence of DIII-VSD activation, consequently altering pore accessibility by mexiletine. From this hypothesis, it was predicted that channels in which the DIII-pore are decoupled from the DIII-VSD by A1326W will exhibit similar mexiletine block. It was observed that, upon the addition of A1326W, mexiletine caused similar TB and UDB for the R1626P, M1652R, and WT channels (FIG. 3B, C).

In the presence of the A1326W mutation, the differences caused by R1626P or M1652R mutation in DIII-VSD activation and SSI are preserved (FIG. 3D, E), suggesting that the A1326W mutation does not interfere with voltage-dependent DIII-VSD conformational changes. A model was proposed to explain the elimination of mexiletine sensitivity by the A1326W mutation in the two LQT3 variants (FIG. 3F). Although R1626P stabilized and M1652R destabilized the activated conformation of DIII-VSD, the channel pore remains in the same conformation with the same mexiletine accessibility, because A1326W decoupled the DIII-pore from the DIII-VSD. These results indicated that the differences in mexiletine sensitivity of R1626P and M1652R are a consequence of the effects of the mutations on DIII-VSD activation, which are transmitted to the DIII-pore to increase accessibility to mexiletine. Thus, removing the coupling between the DIII-VSD and pore abolished the differences in mexiletine sensitivity.

Voltage Dependence of DIII-VSD Activation Determines Mexiletine-Induced Tonic Block (TB)

By studying two LQT variants with extremely high or low mexiletine sensitivity, it was shown that the voltage dependence of DIII-VSD activation strongly affects mexiletine block (Table 2). To determine if this mechanism is generally applicable to common LQT3 variants, it was first investigated how DIII-VSD activation modulates TB by mexiletine. TB is usually assessed at negative potentials (−100 mV), a voltage at which most LQT variants have similar level of inactivation. DIII-VSD activation occurs at much lower voltage range than closed-state inactivation. Consequently, at −100 mV, the variability in the proportion of channels with DIII-VSD in the activated conformation is high among LQT3 variants. The gating properties of WT and 15 LQT3 variant channels and the mexiletine TB of these channels was measured. Most variants analyzed are found in patients who were previously treated with mexiletine. Even though the LQT variants span the channel (FIG. 4A), many of the variants exhibited altered DIII-VSD activation. A strong correlation between the voltage dependence of DIII-VSD activation ($V_{1/2}$ of DIII F-V) and TB by ($R^2$=0.90, FIG. 4B) was observed. Higher TB occurred for channels that had DIII-VSD activation at more negative potentials (FIG. 4B). Instead of a linear relationship, the data was fit to a Hill function, because it was expected that TB will saturate at the ends of the curve. Surprisingly, it was found that the minimum TB saturated at 15% block, suggesting that 15% of mexiletine-mediated TB is lipophilic block (low affinity, voltage-independent block).

The relationship between SSI and TB was investigated to test the classical theory that closed-state inactivation promotes class Ib block. In contrast to DIII-VSD activation, closed-state inactivation ($V_{1/2}$ of SSI) did not correlate well with mexiletine TB ($R^2$=0.48, FIG. 4C). These results further support the hypothesis that voltage dependence of DIII-VSD activation rather than that of closed-state inactivation determines mexiletine TB.

TABLE 2

DIII-VSD activation $V_{1/2}$, SSI $V_{1/2}$, and TB for each LQT3 variants tested in FIGURE 4.

| Variants | DIII-VSD $V_{1/2}$ (mV) | SSI $V_{1/2}$ (mV) | TB |
| --- | --- | --- | --- |
| WT + β1 | −122.0 | −76.2 | 0.207 |
| WT + β3 | −98.0 | −86.0 | 0.163 |
| I397F | −132.0 | −73.4 | 0.253 |
| V411M | −126.4 | −73.8 | 0.234 |
| L771V | −132.3 | −80.0 | 0.261 |
| S941N | −119.6 | −71.4 | 0.148 |
| P1332L | −140.6 | −74.1 | 0.302 |
| ΔKPQ | −128.0 | −85.3 | 0.267 |
| R1623Q | −130.0 | −82.5 | 0.307 |
| R1626P | −165.1 | −120.3 | 0.541 |
| R1644H | −133.0 | −73.7 | 0.297 |
| L1650F | −143.6 | −79.3 | 0.451 |
| M1652R | −102.1 | −65.3 | 0.175 |
| I1771M | −115.0 | −71.9 | 0.180 |
| E1784K | −136.0 | −83.7 | 0.389 |
| A1186T | −128.0 | −79.8 | 0.263 |
| P2006A | −138.0 | −74.3 | 0.334 |

Partial Least-Square Regression Model Predicts Mexiletine Use-Dependent Block and Patients' QTc Shortening UDB is a critical feature of class Ib drugs, because this feature enables the drug to block channels during periods of heightened channel activity, as in tachycardia. Unlike TB, which occurs at resting potentials at which channels undergo limited conformational changes, UDB involves many complex gating transitions, including the activation of the other three VSDs, pore opening, pore closing, channel inactivation, and channel recovery from inactivation. Due to the complexity of the molecular movements that affect UDB, using a single gating parameter, such as SSI or DIII-VSD activation, to predict UDB is insufficient (FIG. 11A). To address this challenge, a data-driven modeling approach was applied to identify the multivariate relationship between channel gating parameters and UDB by mexiletine.

For each LQT variant, 14 gating parameters were quantified that describe gating processes, such as DIII-VSD, DIV-VSD activation, channel activation, and channel fast inactivation (FIG. 5A). The UDB at 250 µM mexiletine for each variant was also assessed. To understand how these gating phenomena related to drug block, a partial least-square (PLS) regression approach was utilized. Gating parameters were used as predictive inputs, and the measured UDB was used as an output for the PLS regression model. PLS regression has the ability to identify relationships between the measured gating parameters and UDB and can reduce redundancy amongst the input parameters Feature selection among the 14 gating parameters was applied to identify the most important parameters in determining mexiletine UDB. Feature selection was based on the VIP (variable importance in projection) score of each parameter, which describes parameter impact on model fitness. Gating parameters with high VIP scores (FIG. 5A bottom, red squares) were extracted to build the final PLS regression model for prediction. The VIP scores suggest that 5 gating parameters are crucial for determining UDB, including voltage dependence of channel conductance ($V_{1/2}$ of G-V), DIII-VSD activation ($V_{1/2}$ of DIII F-V), DIV-VSD activation ($V_{1/2}$ of DIV F-V), time constant of slow recovery from inactivation (slow recovery τ), and late $I_{Na}$. By reducing the number of gating parameters used in the model, feature selection not only helps prevent overfitting but also improves the understanding of the relationship between channel gating processes and drug response.

To reduce data dimensionality, the number of principal components was reduced to 3 because this was sufficient to explain 90% variants in the data. With the selected features and reduced components, the PLS regression model predicts the UDB with a R-squared ($R^2$) of 0.9. The model was further validated with "leave one out" cross-validation. The cross-validated PLS regression model predicts the UDB with a Q-squared ($Q^2$) of 0.7 (FIG. 5B). Compared to the best prediction using a single gating parameter (DIII-VSD activation), which has a $Q^2$ of 0.3, the PLS regression approach improved the prediction accuracy.

A PLS regression model was built to predict mexiletine-induced corrected $QT_c$ shortening ($\Delta QT_c$) in patients with the LQT3 variants for which the channel gating parameters was measure. $QT_c$ interval data was obtained before and after mexiletine for 32 patients with 13 different genetic variants from a previously published study. The VIP scores for $\Delta QT_c$ showed that only two gating parameters are important for determining the $\Delta QT_c$: DIII-VSD activation and τ of slow recovery from inactivation (FIG. 5A bottom). With these two parameters as inputs, the cross-validated PLS regression model predicted $QT_c$ shortening in patients with a Q-square ($Q^2$) of 0.6 (FIG. 5C), demonstrating that the model has significant predictive value. These results indicate that the clinical efficacy of mexiletine can be predicted from measurements of gating parameters of the $Na_V1.5$ variants, supporting the proposal that in vitro testing will help predict a patient's specific response to mexiletine.

This observation was extended by building a precise model for predicting patient specific $QT_c$ shortening by mexiletine based on detailed biophysical parameters.

To validate if the gating parameters selected based on the VIP scores improved the prediction accuracy (model fitness) of the PLS regression models, 1000 models with randomly selected parameters (blue bars, FIG. 12A, 12B) were evaluated. Among these models, those that contain most of the preselected parameters (more than 3 out of 5 for UDB and 1 out 2 for $\Delta QT_c$) had overall improved prediction accuracy, implying that VIP score is an effective method to rank gating parameter importance.

Finally, to facilitate utilization of our predictive model, a mexiletine $QT_c$ shortening calculator user interface was built (FIG. 13). Users can select from a list of previously tested LQT3 variants or enter the channel gating parameters for a new variant, and then input the patient's baseline $QT_c$. The calculator will predict mexiletine shortening of $QT_c$ based on the PLS regression model and output patient's predicted $QT_c$ after mexiletine therapy. If the patients' predicted $QT_c$ after mexiletine is still above 500 ms (high-risk $QT_c^6$), a warning light will illuminate, indicating that mexiletine is unlikely to be a sufficiently effective therapy in preventing arrhythmia events.

Test QTc Shortening Calculator Performance with a Blind Clinical Trial

To test the accuracy of the $\Delta QT_c$ predictions using the PLS regression model, a blind retrospective clinical trial that involved 8 LQT3 patients carrying 5 distinct SCN5A variants was conducted (Table 3, FIG. 6) using not variants included in the training dataset. The 8 patients were previously treated with mexiletine and their electrocardiograms were recorded before and after treatment. Evaluators were blinded from these clinical data during prediction. The $Na_V1.5$ channel variants from those patients were expressed and tested in vitro to obtain the two essential electrophysiological parameters for the prediction: DIII-VSD activation and slow recovery τ. The predicted post-mexiletine $QT_c$ is with the mexiletine $QT_c$ shortening calculator, with an upper and lower bound based on the 95% confidence interval calculated from the cross-validated model.

Seven out 8 patients had post-mexiletine $QT_c$ that aligned with the predictions (Table 3, FIG. 6). It was noted that the one outlier (N1774D) patient that failed to predict correctly had a baseline $QT_c$ of 814 ms, which is higher than most of the training data. Assembling patient data from both training and trial datasets, a trend was observed in that patients with very high $QT_c$ baselines (>650 ms) tend to have higher percentage of $QT_c$ shortening by mexiletine, independent of their genetic variants (FIG. 14). As a result, the current model is not suitable for predicting patients with very high baseline $QT_c$ (>650 ms). From this blind clinical trial, the PLS model accurately predicted patients' response to mexiletine therapy for those patients with a baseline lower than 650 ms.

TABLE 3

Mexiletine $QT_c$ calculator trial outcomes.

| Genetic Variants | baseline $QT_c$ | Measured post mex $QT_c$ | Predicted post mex $QT_c$ | Prediction lower bound | Prediction upper bound |
|---|---|---|---|---|---|
| F1473S | 550 | 491 | 488 | 452 | 523 |
| I1768V | 520 | 503 | 499 | 465 | 520 |
| K1500del | 478 | 434 | 415 | 384 | 446 |
| K1500del | 500 | 430 | 434 | 401 | 466 |
| K1500del | 493 | 463 | 428 | 396 | 460 |
| K1500del | 494 | 434 | 429 | 397 | 461 |
| L1608P | 604 | 480 | 518 | 479 | 558 |
| N1774D | 814 | 610 | 750 | 697 | 803 |

The ability of PLS regression model to predict UDB with LQT3 variants that were not used for training the model was also tested. Using the critical gating parameters that were identified, the model accurately predicted UDB by mexiletine with Pearson correlation R of 0.82 (FIG. 15).

Examples for Arrhythmias Including Ventricular Tachycardia and Ventricular Fibrillation.

Methods for evaluating Nav1.5 function by VCF have been disclosed herein (FIG. 16). During these experiments, the membrane potential, Vm, was set to different levels, and ionic currents were measured with the cut-open oocyte method. The result is rapid clamping of the membrane voltage (<100 μs) that enables the resolution of fast components of Nav channel gating. Changes in VSD conformation are simultaneously reported by a cysteine-tethered fluorophore, TAMRA-MTS. When the protein moves, the local environment around the fluorophore changes, thereby altering the magnitude of its fluorescence emission. By tracking the change in fluorescence magnitude ($\Delta F$), the kinetics of VSD conformational changes can be monitored. VCF requires very high levels of channel expression. Compared with Nav1.4, the density of wildtype Nav1.5 expressed in oocytes is too low for VCF. To increase expression, the Nedd4 ubiquitination motif (Y1977A) on the C-terminus was ablated, which increased the current and produced a fluorescence change that was large enough to resolve for the fluorophore-tethered DII-VSD (S805C). Scanning the S3-S4 loops, V215C (DI), M1296C (DIII), and S1618C (DIV) were identified as labeling sites on each domain. With the ability to monitor the transitions of Nav1.5, how anti-arrhythmic molecules interact with the channel was explored. The results showed that mexiletine stabilized DIII-VSD in the activated conformation (FIG. 1D), whereas the other domains were mostly unaffected.

Previous work has shown that patients with different LQT3-linked variants had distinct responses to mexiletine. To test whether the variant effect on the DIII-VSD correlated with drug block, 13 variants were introduced into the M1296-Y1977A background (FIG. 17). A striking connection was found between the membrane potential at which half of the DIII-VSDs are activated (V1/2) and tonic block (FIG. 4B). Given this strong correlation, a strategy to predict the expected change in QT interval from the effect of a specific mutation on DIII-VSD was devised. The strategy employed variable importance in projection (VIP) scores to reveal the most predictive parameters of an initial regression model, which revealed that the slow time constant of inactivation recovery could be combined with the DIII-VSD V1/2 for activation to predict the change in corrected QT interval (QTc). Leave-one-out cross-validation of the partial least squares regression (PLSR) model using these two variables led to compelling Q2 (crossvalidated R2) value of 0.6 (FIG. 5). To test the model, several new patients, whose data were not included in the training set, were evaluated. This small pilot trial demonstrated that the change in QTc could be accurately predicted as evidenced by such occurred for 7 out of 8 patients (FIG. 6). The only patient who fell outside of the predicted range had a QTc of 814 ms, suggesting that there is a different response when the QT interval is extremely prolonged. The ability of LQT3 variants to impact mexiletine response implies that common variants may also determine whether mexiletine is therapeutically effective in VT/VF patients.

Common variants of Nav1.5 typically occur in the intracellular portions of the channel: R34C (N-terminal), H558R and S524Y (DI-DII linker), and S1103Y (DII-DIII linker). The most abundant splice isoform of Nav1.5 has a deletion of Q1077 (Q-del), which is in the DII-DIII linker. Because there is no selective evolutionary pressure to maintain sensitivity to anti-arrhythmic drugs, whether there are variants with nonpathological kinetics but an altered response to anti-arrhythmic molecules was investigated.

To perform the investigation, lidocaine block of two common variants S1103Y and Qdel in the HEK cell expression system was evaluated. While Q-del was notably unaffected, S1103Y, a variant commonly found in African Americans, displayed a 30% increase in tonic block and a 17% increase in use-dependent block, demonstrating that common variants have the potential to significantly affect therapeutic outcomes (FIG. 18). Accordingly, other sodium ion channel blockers such as mexiletine experiments will perform similarly given the similarity of the molecules.

The detailed molecular mechanisms of Nav1.5 regulation by intrinsically disordered linkers were then examined.

The most common variants of Nav1.5 (R34C, S524Y, H558R, and S1103Y) and phosphorylation sites are all located within the intracellular domains. However, because these domains are disordered, they are not resolved in recent Nav channel structures. To understand how sequence variation and posttranslational modification regulate loop dynamics, recent advances in the simulation of intrinsically disordered proteins that predict how altered sequence will affect conformational dynamics were used. The CAMPARI software suite was used for this purpose. The software utilizes Monte Carlo simulations of the loops with an implicit solvation model, which simplifies the simulation by treating the surrounding water as a continuous medium.

The distribution of charged residues is of great importance when investigating disordered proteins, as it is highly predictive of conformational ensemble. For example, a protein with highly segregated positive and negative charges will tend to prefer hairpin-like conformations. Our initial evaluation of the loops using the Classification of Intrinsically Disorder Ensemble Regions (CIDER) webserver predicts that the DI-DII and DII-DIII loops are Janus sequences, which can be either collapsed or expanded, depending on context. This is a compelling observation, because the loops are highly regulated by post-translational modifications that could readily shift the balance between collapsed or expanded conformations.

To test whether the simulation approach could recapitulate experimental findings, mass spectrometry was used to identify phosphorylation sites on the α subunit of Nav1.5. The initial results show that native Nav1.5 channels, purified from mouse left ventricles, carry more than 40 phosphorylation sites. Interestingly, some of these phosphorylation sites are clustered, and four of these were found in the DI-DII linker. Out of these clusters, the phosphosilent or phosphomimetic mutations of the S664, S667, T670 to S671 cluster uniquely alter the gating kinetics of Nav1.5 (FIG. 19).

To test the computational approach, the effects of phosphomimetic mutations within segments representing two of these clusters, 441-480 and 651-684, were simulated. As shown in FIG. 18C, introducing charges into the S664-S671 cluster leads to a substantial change in the regional conformational ensemble, consistent with experimental results in FIG. 18B that reveal a Nav1.5 gating effect for only the 651-684 segment.

Induced Pluripotent Stem Cell (iPSC) Derived Cardiomyocytes as a Drug Response Model.

Recently, iPSC derived cardiomyocytes (iPSC-CMs) have been used to model QT prolongation by inherited mutations and off-target pro-arrhythmic side effects of chemotherapy molecules. iPSC-CMs will therefore be a useful model for mechanistically probing the connection between the patient mexiletine response and predictors, such as β-adrenergic tone and genetic variant. Using established protocols, iPSC-CMs expressing the GCaMP6 Ca2+ reporter that was knocked into the first exon of the AAVS1 "safe harbor" locus, were differentiated. Fluorescence images of ACNT2 and nuclei revealed clearly defined sarcomeres in iPSC-CM (pictures not shown). The cells generate action potentials and robust Na+ currents (FIG. 19A). Field potential durations (FIG. 19B), which are representative of the QT interval on the electrocardiogram with a multi-electrode array, were also measured.

Many patients who are treated with mexiletine are also prescribed a β-blocker, and Nav1.5 gating is known to be affected by β-adrenergic stimulation. Thus, whether lidocaine block would be modulated by application of cAMP was tested. Consistent with previous observation, cAMP hyperpolarizes Nav1.5 activation and inactivation. In addition, use dependent block kinetics are accelerated, suggesting that adrenergic tone and its modulation by β-blockers may significantly affect the mexiletine response.

Based on this data, which demonstrates the premise and feasibility, a mexiletine response model is developed. This model uses at least one parameter selected from the group of common genetic variants, phosphorylation due to β-adrenergic stimulation, interaction with amiodarone, genetic variability, phosphorylation state, and any combination thereof to predict response to sodium ion channel blockers, such as lidocaine and mexiletine. Advantageously, as the amount of data increases, an optimized iPSC-CM model of the sodium ion channel blocker (such as mexiletine) can be used to probe cases where the model failed, with the aim of discovering novel regulators and iteratively improving the model.

The present disclosure will also permit the determination of how the intracellular loops of Nav1.5 regulate its gating and pharmacology and identify Nav1.5 sites that are differentially phosphorylated in the presence of β-adrenergic stimulation. Such information will be valuable to continually improve the predictive response model.

While putative sites on Nav1.5 that are linked to β-adrenergic stimulation have been biochemically identified, their ablation with phosphosilent mutations does not fully remove the response to β-agonists. Fully ablating the Nav1.5 response to a β-agonist requires the additional elimination of endoplasmic reticulum retention sites, suggesting a complex regulation mechanism. To identify the in vivo phosphorylation sites involved in the β-adrenergic regulation of Nav1.5 channels, mass spectrometry (MS)-based phosphoproteomic analyses will be undertaken on channels purified from the left ventricles of isolated perfused and working mouse hearts in the presence or absence of β-adrenergic stimulation. Isolated working hearts will be treated (or not, in control conditions) with isoproterenol (ISO; 0.3 μM) to identify those Nav1.5 sites that are phosphorylated after β-adrenergic receptor activation. A specific PKA inhibitor (PKI; 1 μM) will be used to delineate the PKA-dependent sites. Larger samples from intact hearts are required due to the large quantity of Nav1.5 channel protein required for MS analyses. The working heart allows recapitulation of physiological afterload and preload conditions, which are likely to regulate the β-adrenergic signaling cascade. A second set of MS analyses will also be undertaken from Nav1.5 channels purified from non-failing left ventricular human biopsies, obtained from human donors through the Washington University Translational Cardiovascular Biobank and Repository (TCBR). These analyses from human samples will allow comparison and verification that the phosphorylation sites identified from mouse Nav1.5 channels are conserved in human. Nav1.5 channels will be purified from both samples via immunoprecipitation using a monoclonal anti-NavPAN specific antibody, and the post-translational modifications will be identified by MS. In addition, the use of tandem-mass-tag 10 (TMT10) labeling will be employed to allow MS quantification of many phosphorylation sites under different experimental conditions. All protocols and corresponding analyses of MS data will exploit well established and validated approaches used routinely in both laboratories, and no technical or interpretation difficulties are anticipated.

Electrophysiological experiments will then be undertaken to characterize the roles of newly MS-identified Nav1.5 phosphorylation sites in mediating the β-adrenergic and PKA-dependent regulation of Nav1.5 channels. These whole cell voltage-clamp analyses will be performed on freshly isolated neonatal mouse ventricular myocytes in which the expression of endogenous Nav1.5 will be eliminated transiently by knockdown using short hairpin RNA (shRNA)-expressing adenoviruses, and simultaneously rescued with wildtype or phosphomutant human Nav1.5 adenoviruses. The same adenoviral tools will then be used in iPSCCMs to determine how these phosphorylation sites participate in the sodium ion channel blocker (such as mexiletine) response.

Additionally, the disclosure permits the connection of variant, phosphorylation and drug block to VSD dynamics. It is compelling that all the common Nav1.5 variants and its phosphorylation occur on the disordered intracellular loops, which cannot be resolved with cryo-electron microscopy. Accordingly, this information will be used to further develop computational methods to discover mechanisms that enable genetic and post-translational modifications in these loops to regulate channel gating.

In the data herein, CAMPARI software was used to simulate segments of the DI-DII linker (FIG. 19) and assess how novel phosphorylation site clusters impact loop dynamics. While these simulations were successful for the two clusters tested, they are limited in that the ends of the segments were able to float freely in solution. In a channel, at least one end of the segment will be tethered, either to an adjacent disordered segment, a transmembrane helix, or a binding site for an accessory subunit, which may carry a tethered protein. While the simulations provide valuable insight into the local interactions within the segment, the tethering at one or both ends may significantly alter its dynamics. Thus, the current disclosure contemplates integrating these potential tethers for the DI-DII linker, including with the transmembrane helices at either end and with the binding of 14-3-3, which was recently shown to participate in channel dimerization. By accounting for the reduced mobility and interaction potential of residues that are near to membrane-embedded helices or bound proteins, the predictive capability of the simulations will be improved.

As the simulation methods are developed, they will be applied to discover how each of the common variants and phosphorylation sites affects the dynamics of the loop they reside in. As in preliminary data (FIG. 19B), it is expected that greater changes in the average conformational ensemble of a simulated segment will reflect a greater impact of the variant or phosphorylation event. To test the predictive ability of the model, charged and neutral amino acids will be experimentally introduced or removed at locations predicted by the simulations to cause large or no change in the conformational ensemble. VCF (FIG. 16) will then be used to measure whether the ionic current or the VSDs are affected by the introduced mutation. Accordingly, the introduction or removal of charged and/or neutral amino acids and the resulting impact on the conformational ensemble will be encompassed by this disclosure. An advantage to using the fluorescent method is that while the introduced mutations may cause subtle changes in ionic current kinetics, they may cause a large change in VSD activation, which will be detectable.

Additionally, the introduction of point mutations will permit the improvement of the model parameters, with additional mutations, predicted by the simulation, serving as test data. This process will further enhance the predictive accuracy of the model. Next, the most common Nav1.5 variants: R34C (N-terminal), S524Y and H558R (DI-DII Linker), and S1103Y (DII-DIII Linker) will be simulated to probe how they alter linker dynamics and they will also be examined with the VCF protocols to determine how they are regulating the VSDs. As it was already shown that S1103Y modulates mexiletine sensitivity (FIG. 19), it is expected that it will significantly affect the voltage-dependence of the DIII-VSD.

As results from the MS analysis begin to arrive, the effect of phosphorylation due to β-adrenergic stimulation will be simulated, in addition to probing how it regulates the VSDs with VCF. The aim will be to understand how changes in phosphorylation alter the mexiletine response of the channel. In addition, it is predicted that variants that co-inhabit the intracellular loops will alter β-adrenergic regulation of the channel. This prediction will be verified with both the simulation method and by introducing the variants simultaneously with phosphomimetic mutations for VCF experiments.

Finally, how amiodarone impacts the VSDs will be measured. As many patients are simultaneously treated with both mexiletine and amiodarone, its presence is predicted to be a confounding variable. To enable better prediction, the amiodarone impact on the Nav1.5 VSDs will be measured, as in FIG. 16. Next, whether mexiletine and amiodarone work additively to affect Nav1.5 current and gating will be determined. Together, these experiments will provide key insight into the mechanisms of variant, post-translational and drug regulation of Nav1.5. The biophysical parameters that are measured will provide the basis for a predictive model of the patient mexiletine response in Aim 2.

The present disclosure provides a model that accurately predicts how variants and post-translational modifications will affect patient response. In preliminary data (FIG. 17), it was demonstrated that variant-linked changes in biophysical parameters (DIII-VSD V1/2 and slow time constant of inactivation recovery) can predict whether QTc is shortened by mexiletine. These same or a similar set of parameters exists to predict whether patients with ventricular arrhythmia will respond to mexiletine. The key data demonstrates that common variants, amiodarone and β-adrenergic stimulation alter Nav1.5 ionic current and VSD kinetics. Patient outcomes, including change in QTc, frequency of ventricular ectopic depolarization, and reduction in arrhythmia burden, can be predicted by the model disclosed herein and by a model whose input is the biophysical parameters associated with increased β-adrenergic tone and genetic variation.

To build this predictive model, the approach that was used in FIG. 17, where feature selection (variable importance in projection (VIP) scores) was used to reveal the most predictive parameters of an initial set, which would include biophysical measures of variant-linked voltage and time-dependence of both the VSDs and the ionic current, in addition to clinical parameters such as heart rate and pNN50.

In another aspect, the extent to which an iPSC-derived model recapitulates Nav1.5 pharmacology effects will be tested in order to model patient drug response with iPSC-CMs, such as was demonstrated in FIGS. 17 and 18. This will verify that the iPSC-CM model is capable of recapitulating the dependence of mexiletine block on the genetic variation and phosphorylation that was observed in the preliminary data (FIGS. 17,18). To begin, 6 variants will be introduced across the spectrum of predicted drug response into iPSC lines. Since change in patient QTc is dependent on two variables, DIII-VSD V1/2 and the slow time constant of inactivation recovery, variants that display significant differences in each of these (Table 4) were selected.

TABLE 4

| Variant | DIII-VSD V½ (mV) | Slow recovery time (ms) |
| --- | --- | --- |
| WT | −122.0 | 52.3 |
| M1652R | −102.1 | 19.1 |
| I1771M | −115.0 | 42.7 |
| S941N | −119.6 | 47.8 |
| E1784K | −136.0 | 79.7 |
| L1650F | −143.6 | 39.9 |
| R1626P | −165.1 | 60.7 |

Verified iPSC lines that are homozygous for the edited SCN5A, will be differentiated into cardiomyocytes as in FIG. 20. Tonic and use dependent block of the Na current in each of these will be measured and compared to previous recordings in *Xenopus laevis* oocytes and HEK cell expression systems to quantify the direct effect of the variants on the interaction of mexiletine with Nav1.5. Significant differences in comparison to the expression system suggest that the composition of the macromolecular Nav1.5 complex in the iPSC-CMs is affecting mexiletine interaction or that other channels, such as Nav1.1, or other Nav1.5 channel isoforms may be affecting the measurement. While large differences in the blocking parameters of the iPSC-CMs compared to the expression cell data, their discovery are not expected, they would present an opportunity to probe additional factors that may affect drug block, including the β-subunits and intracellular fibroblast growth factors.

Cellular and tissue level variant impacts will be assessed by culturing iPSCCMs onto a multi-electrode array to assess the change in field potential duration (FPD), which is a correlate of QT interval, with and without the addition of mexiletine. Once iPSC-CMs are plated and a control FPD has been recorded, mexiletine will be applied and the predicted change in QTc to the FPD that has been corrected for beating rate (FPDc) will be compared. If the drug block parameters resemble those that were measured in oocytes and HEK cells, then the mexiletine-induced change in FPDc to correlate with QTc change that is predicted from Nav1.5 biophysical parameters that correlate with the patient response will be compared, validating the usefulness of the iPSC model.

The iPSC-CM model will also be used to investigate clinical study conditions. As iPSC-CMs contain many of the currents that are found in human ventricular myocytes, the model will allow an improvement of the understanding of the amiodarone interaction with mexiletine to further improve the ability of the predictive model to account for the interaction in patients. The cellular effects of the amiodarone-mexiletine interaction both with traditional electrophysiology methods and in monolayers with MEA protocols will be characterized.

For patients who do not respond as predicted, these iPSCs will be differentiated into cardiomyocytes using the optimized protocol from the previous sub-aim and their mexiletine response will be evaluated. If the patient does not carry variant 1 of SCN5A (as in WT-C iPSCs), a 2nd line will be created by CRISPr editing the control iPSCs to carry the patient variant. These lines will be compared, and if their drug response differs, it will be concluded that patient background contributes to the drug response. A full complement of experimental methods will then be used to probe the mechanism. This can begin by recording Na+ current block parameters to test whether the difference is due to changes in Nav channel pharmacology. If this is the case, then the exome data should be analyzed to determine whether any accessory proteins carry variants that might affect the current. The phosphorylation state of the channel will also be investigated using mass spectrometry methods. Conversely, if the Na+ current and its block by mexiletine is not significantly different, then other aspects are contributing to the drug response and the currents of the cell with patch clamp recordings and Ca2+ dynamics with fluorescent probes will be characterized. By identifying which currents are changed to affect FPD, the potential causes of the differences will be significantly decreased. Next, RNAseq (see LOS from McDonnell Genome Institute) will be used to measure how message RNAs that are related to the altered current are affected, providing a route toward identifying additional proteins regulate the mexiletine response.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A method for predicting a patient response to a sodium ion channel blocker, the method comprising:
    receiving, at a user interface, a plurality of parameters associated with sodium ion channels of the patient, wherein the plurality of parameters associated with sodium ion channels of the patient comprise DIII-VSD activation and slow recovery τ from inactivation;
    applying one or more inputs to a supervised machine learning model, the one or more inputs comprising the plurality of parameters associated with the sodium ion channels of the patient, the model being previously trained using historical data, the historical data comprising ion channel gating parameters associated with sodium ion channels and their corresponding patient response to a sodium ion channel blocker;

receiving one or more outputs from the model, at least one of the one or more outputs including a predicted patient response to the sodium ion channel blocker;

transmitting, for display on the user interface, the one or more outputs from the model;

updating the historical data to include the plurality of parameters associated with the sodium ion channels of the patient and the corresponding one or more outputs; and re-training the model using the updated historical data.

2. The method according to claim 1, wherein the plurality of parameters further comprise ion channel gating parameters selected from a group consisting of activation rate, deactivation rate, voltage dependence of activation, voltage dependence of inactivation, inactivation rate, inactivation recovery rate, VSD activation rate, VSD deactivation rate, VSD voltage-dependence, and any combination thereof.

3. The method according to claim 1, wherein the plurality of parameters further comprise ion channel gating parameters selected from a group consisting of DIII-VSD V1/2, DIII deactivation t, Steady-state Inactivation, inactivation at resting, inactivation t, fast recovery t, slow recovery contribution, late INa, late INa at 150 ms, DIV-VSD V1/2, DIV-VSD activation τ, and any combination thereof.

4. The method according to claim 3, wherein the plurality of parameters are DIII-VSD V112 and slow recovery τ.

5. The method according to claim 1, wherein the model exhibits a PLS cross-validated Q2 of at least 0.6.

6. The method according to claim 1, wherein the model exhibits a PLS cross-validated Q2 of at least 0.9.

7. The method according to claim 1, wherein the patient response is calculated as a ΔQT as measured by an electrocardiogram.

8. The method according to claim 1, wherein the sodium ion channel blocker is selected from a group consisting of ranolazine, phenytoin, disopyramide, lidocaine, mexiletine, triamterene, lamotrigine, amiloride, moricizine, oxcarbazepine, quinidine, procainamide, tocainide, amiodarone, propafenone, eleclazine, flecainide, encainide, ajmaline, aprindine, tetrodotoxin, eslicarbazepine acetate, pilsicainide, and eslicarbazepine.

9. The method according to claim 8, wherein the sodium ion channel blocker is mexiletine.

10. The method of claim 1, wherein the patient has LQT syndrome or an arrhythmia.

11. The method of claim 10, wherein the arrhythmia is ventricular tachycardia or ventricular fibrillation.

12. An in vitro method for predicting a patient response to a sodium ion channel blocker, the method comprising:
collecting a biological sample from a patient;
expressing at least one gene from the biological sample;
testing the expressed gene for a plurality of parameters; and
using the plurality of parameters in the model according to claim 1 to predict the patient response to the sodium ion channel blocker.

13. The method according to claim 12, wherein the patient has LQT syndrome or an arrhythmia.

14. The method according to claim 12, wherein the at least one gene expresses $Na_v1.5$.

15. The method according to claim 12, wherein the plurality of parameters are ion channel gating parameters selected from a group consisting of activation rate, deactivation rate, voltage dependence of activation, voltage dependence of inactivation, inactivation rate, inactivation recovery rate, VSD activation rate, VSD deactivation rate, VSD voltage-dependence, and any combination thereof.

16. The method of claim 12, wherein the plurality of parameters further comprise ion channel gating parameters selected from a group consisting of fraction of DIII-VSD activated at resting, DIII-VSD V1/2, DIII deactivation τ, Steady-state Inactivation, inactivation at resting, inactivation τ, inactivation fast recovery τ, slow recovery τ, slow recovery contribution, late INa, late INa at 150 ms, DIV-VSD V1/2, DIV-VSD activation τ, and any combination thereof.

17. The method according to claim 12, wherein the patient response is calculated as a ΔQT as measured by an electrocardiogram.

18. The method according to claim 12, wherein the sodium ion channel blocker is selected from a group consisting of ranolazine, phenytoin, disopyramide, lidocaine, mexiletine, triamterene, lamotrigine, amiloride, moricizine, oxcarbazepine, quinidine, procainamide, tocainide, amiodarone, propafenone, eleclazine, flecainide, encainide, ajmaline, aprindine, tetrodotoxin, eslicarbazepine acetate, pilsicainide, and eslicarbazepine.

19. The method according to claim 18, wherein the sodium ion channel blocker is mexiletine.

20. The method according to claim 12 wherein an arrhythmia is ventricular tachycardia or ventricular fibrillation.

\* \* \* \* \*